US012582728B2

(12) United States Patent
Pillarsetty et al.

(10) Patent No.: US 12,582,728 B2
(45) Date of Patent: Mar. 24, 2026

(54) THERANOSTIC AGENTS FOR PSMA POSITIVE CANCERS

(71) Applicant: Memorial Sloan Kettering Cancer Center, New York, NY (US)

(72) Inventors: Naga Vara Kishore Pillarsetty, New York, NY (US); Teja Muralidhar Kalidindi, New York, NY (US); Sang Gyu Lee, New York, NY (US); Steven M. Larson, New York, NY (US); Jason S. Lewis, New York, NY (US); Serge Lyashchenko, New York, NY (US); Eva Burnazi, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 915 days.

(21) Appl. No.: 17/638,512

(22) PCT Filed: Aug. 28, 2020

(86) PCT No.: PCT/US2020/048524

§ 371 (c)(1),
(2) Date: Feb. 25, 2022

(87) PCT Pub. No.: WO2021/041896

PCT Pub. Date: Mar. 4, 2021

(65) Prior Publication Data

US 2022/0305149 A1 Sep. 29, 2022

Related U.S. Application Data

(60) Provisional application No. 62/894,594, filed on Aug. 30, 2019.

(51) Int. Cl.

| | |
|---|---|
| ***A61K 51/10*** | (2006.01) |
| ***A61K 33/243*** | (2019.01) |
| ***A61K 49/00*** | (2006.01) |
| ***A61K 51/04*** | (2006.01) |
| ***A61P 35/00*** | (2006.01) |

(52) U.S. Cl.
CPC ........ *A61K 51/1045* (2013.01); *A61K 33/243* (2019.01); *A61K 49/0002* (2013.01); *A61K 51/0497* (2013.01); *A61P 35/00* (2018.01)

(58) Field of Classification Search
CPC .............. A61K 51/1045; A61K 33/243; A61K 49/0002; A61K 51/0497; A61P 35/00
See application file for complete search history.

(56) References Cited

U.S. PATENT DOCUMENTS

2016/0256579 A1 9/2016 Shalom
2018/0236110 A1 8/2018 Pomper et al.

FOREIGN PATENT DOCUMENTS

EP 3 064 224 A1 9/2016

OTHER PUBLICATIONS

Zechmann et al. "Radiation dosimetry and first therapy results with a 124I/131 I-labeled small molecule (MIP-1095) targeting PSMA for prostate cancer therapy", Eur J Nucl Med Mol Imaging (2014), 41:1280-1292, DOI: 10.1007/s00259-014-2713-y.
Cardinale et al., "Preclinical Evaluation of 18F-PSMA-1007, a New Prostate-Specific Membrane Antigen Ligand for Prostate Cancer Imaging", The Journal of Nuclear Medicine. vol. 58 p. 425-431 (Mar. 2017).
International Search Report and Written Opinion dated Jan. 26, 2021 on P.C.T. Application No. PCT/US2020/048524.
Lutje et al., "PSMA ligands in prostate cancer-Probe optimization and theranostic applications", Methods. vol. 130 p. 42-50 (2017).

*Primary Examiner* — Robert S Cabral
(74) *Attorney, Agent, or Firm* — Foley & Lardner LLP

(57) ABSTRACT

The present disclosure provides compositions and methods for the detection and treatment of cancer. Specifically, the compositions of the present technology include novel radio-halogenated (e.g., radioiodinated) PSMA targeting agents and methods of using the same in diagnostic imaging as well as radiation therapy.

19 Claims, 17 Drawing Sheets

PSMA11

HPLC Sample: $^{131}$I-PSMA-11-081820-02

DA-220nm Chromatogram

DA-220nm Table

| Name | Retention (min) | Area (mAU·s) | %ROI (%) | Concentration |
|---|---|---|---|---|
| ascorbate | 3.07 | 67819.4 | 100.00 | |
| 1 Peak | | 67819.4 | 100.00 | |

$^{131}$I Chromatogram $^{131}$I Table

| Name | Retention (min) | Area (Counts) | %ROI (%) |
|---|---|---|---|
| Free 131I | 3.17 | 825 | 3.43 |
| 131I-MSK-PSMA-1 | 9.05 | 22812 | 95.03 |
| Impurity | 11.07 | 368 | 1.53 |
| 3 Peaks | | 24005 | 100.00 |

HPLC Sample: $^{131}$I-PSMA-11-081820 @ 18 hrs. post-EOS

DA-220nm Chromatogram

DA-220nm Table

| Name | Retention (min) | Area (mAU·s) | %ROI (%) | Concentration |
|---|---|---|---|---|
| ascorbate | 3.05 | 68697.7 | 100.00 | |
| 1 Peak | | 68697.7 | 100.00 | |

$^{131}$I Table

| Name | Retention (min) | Area (Counts) | %ROI (%) |
|---|---|---|---|
| Region 1 | 3.17 | 1097 | 4.95 |
| 131I-PSMA-11 | 9.03 | 20607 | 92.90 |
| Region 2 | 10.37 | 232 | 1.05 |
| Region 3 | 10.70 | 246 | 1.11 |
| 4 Peaks | | 22183 | 100.00 |

HPLC Sample: $^{131}$I-PSMA11-081820-02@45 hrs

DA-220nm Chromatogram

DA-220nm Table

| Name | Retention (min) | Area (mAU·s) | %ROI (%) | Concentration |
|---|---|---|---|---|
| Ascorbate | 2.90 | 68373.4 | 100.00 | |
| 1 Peak | | 68373.4 | 100.00 | |

$^{131}$I Table

| Name | Retention (min) | Area (Counts) | %ROI (%) |
|---|---|---|---|
| Free 131I | 3.17 | 1569 | 7.58 |
| 131I-PSMA11 | 9.15 | 18925 | 91.44 |
| Region 1 | 11.17 | 203 | 0.98 |
| 3 Peaks | | 20697 | 100.00 |

THERANOSTIC AGENTS FOR PSMA POSITIVE CANCERS

CROSS-REFERENCE TO RELATED-APPLICATIONS

This application is a U.S. National Stage Application under 35 U.S.C. § 371 of International Patent Application No. PCT/US2020/048524, filed on Aug. 28, 2020, which claims the benefit of and priority to U.S. Provisional Patent Application No. 62/894,594, filed Aug. 30, 2019, the entire contents of each of which are incorporated herein by reference.

TECHNICAL FIELD

The present technology relates generally to compositions including radiohalogenated PSMA agents, including radioiodinated PSMA targeting agents and methods of using the same in diagnostic imaging as well as radiation therapy.

BACKGROUND

The following description of the background of the present technology is provided simply as an aid in understanding the present technology and is not admitted to describe or constitute prior art to the present technology.

Prostate cancer is the most commonly diagnosed cancer and the second leading cause of cancer death among men in the United States. PSMA is a type II transmembrane protein that is over-expressed in prostate cancer, including advanced and metastatic disease as well as in renal tubules, bladder carcinoma, and in the tumor neovasculature of many solid tumors. While several radioiodinated PSMA targeting agents have shown promise as theranostics, such agents generally involve multi-step synthesis including acid catalyzed deprotection. These preparation methods are associated with diminished yields, making it difficult and impractical to produce therapeutic doses of radioiodinated PSMA targeting agents.

SUMMARY OF THE PRESENT TECHNOLOGY

In one aspect, the present disclosure provides radiolabeled PSMA ligands, including radiolabeled PSMA ligands for imaging and radiation therapy. For example, there are provided compounds of Formula I, stereoisomers thereof, or pharmaceutically acceptable salts of the compounds or stereoisomers thereof:

I

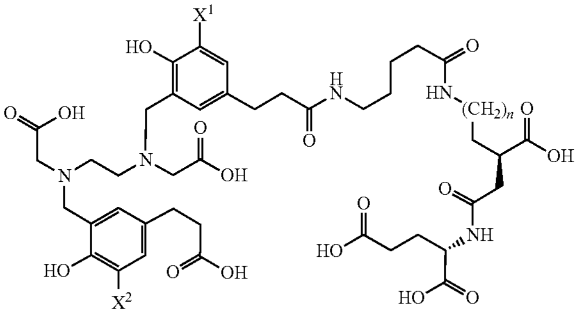

wherein, $X^1$ and $X^2$ are independently selected from the group consisting of H, I, Br, At, a radioisotope of Br (Br*), a radioisotope of I (I*), and a radioisotope of At (At*), provided at least one of $X^1$ and $X^2$ is not H; and n is 1, 2, 3, or 4. In any embodiments, the radioisotope of Br*, I* and At* may be selected from $^{76}$Br, $^{77}$Br, $^{82}$Br, $^{123}$I, $^{124}$I, $^{125}$I, $^{131}$I, or $^{211}$At. In any embodiments $X^1$ and $X^2$ may be independently selected from the group consisting of H, I, and a radioisotope of I(I*), provided at least one of $X^1$ and $X^2$ is not H.

In any embodiments of the compounds herein, $X^1$ may be H. In any embodiments $X^2$ may be H. In any embodiments $X^1$ and $X^2$ may both be I (non-radiolabeled iodine) or a mixture of I and I*. In any embodiments, $X^1$ may be I, I* or a mixture thereof. In any embodiments, $X^2$ may be I, I* or a mixture thereof. In any embodiments $X^1$ and $X^2$ may both be Br (non-radiolabeled bromine) or a mixture of Br and Br*. In any embodiments, $X^1$ may be Br, Br* or a mixture thereof. In any embodiments, $X^2$ may be Br, Br* or a mixture thereof. In any embodiments $X^1$ and $X^2$ may both be At (non-radiolabeled astatine) or a mixture of At and At*. In any embodiments, $X^1$ may be At, At* or a mixture thereof. In any embodiments, $X^2$ may be At, At* or a mixture thereof.

In any embodiments, the compound of Formula I may be a compound of Formula IA, IB, or IC, a stereoisomer thereof, or a pharmaceutically acceptable salt of the compound or stereoisomer thereof:

IA

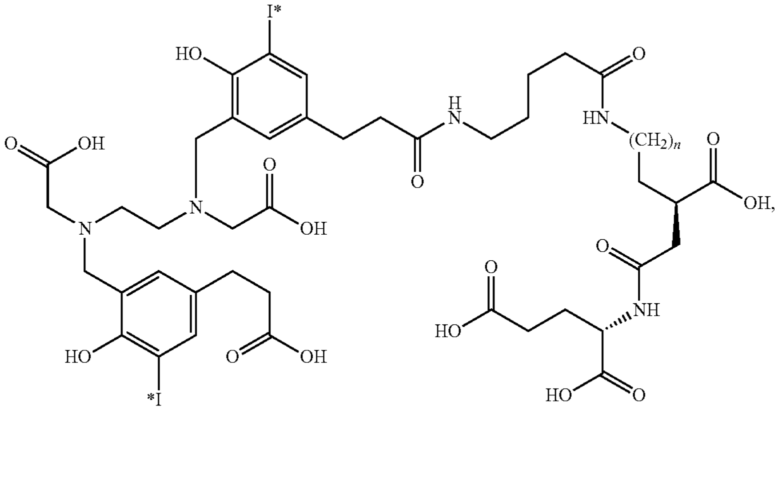

-continued

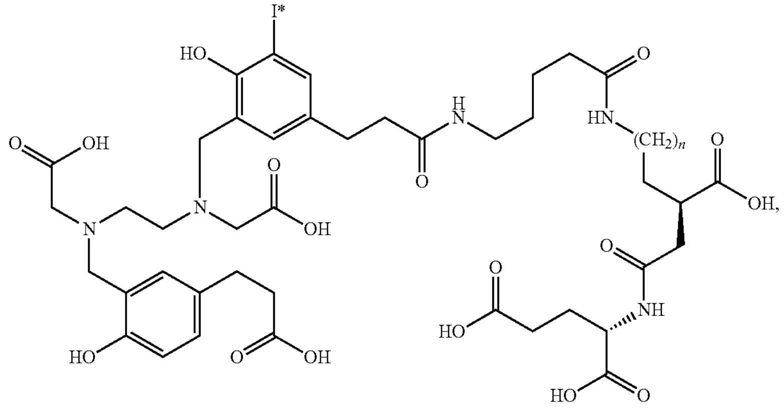

IB

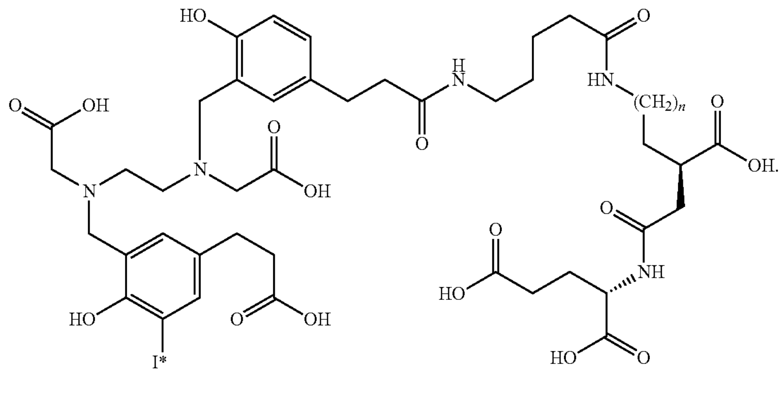

IC

In any embodiments of the compounds disclosed herein (including but not limited to compounds of Formulas I, IA, IB, and IC), n may be as noted above, 1, 2, 3, or 4. In any embodiments of the compounds herein n may be 3. Thus in certain embodiments, the compounds may be compounds of Formulas ID, IE or IF, stereoisomers thereof or pharmaceutically acceptable salts of the compounds or the isomers thereof:

ID

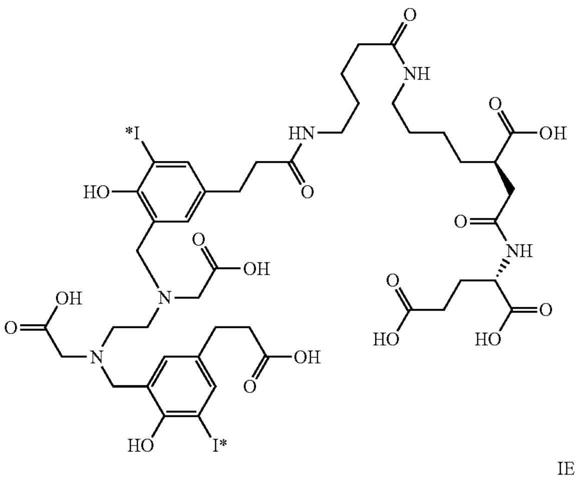

IE

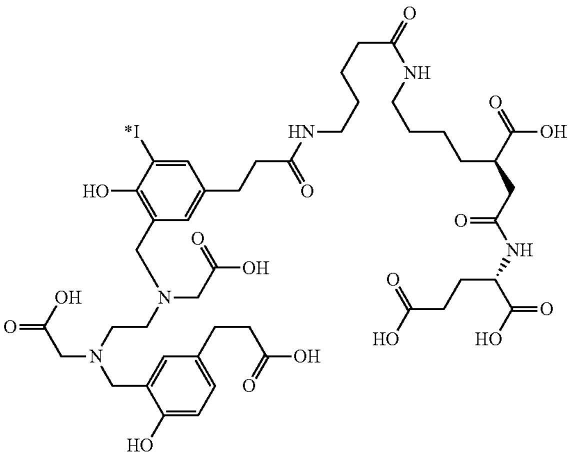

IF

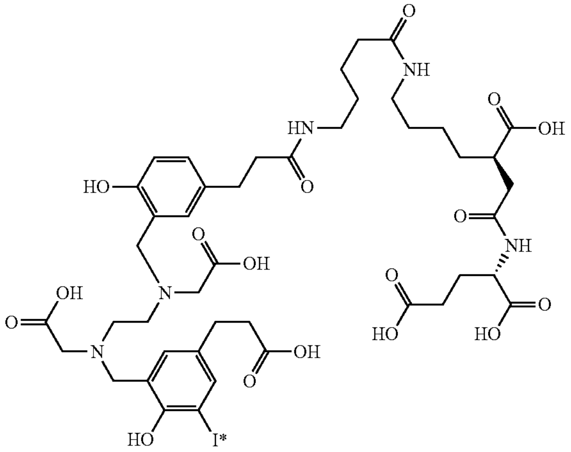

In any embodiments of compounds herein (including but not limited to compounds of Formulas I, IA, IB, IC, ID, IE, and IF), the radioisotope of I* may be selected from $^{123}I$, $^{124}I$, $^{125}I$, or $^{131}I$. In any embodiments, the radioisotope of I* may be $^{131}I$.

In another aspect, the present technology provides compositions including the compounds, e.g., compositions including any two or more compounds disclosed herein, such as, but not limited to compounds of Formulas I, IA, IB, IC, ID, IE, IF, and IE. As further non-limiting examples, the compositions may include compounds of Formulas IA and IB, IA and IC, or IA, IB and IC. Likewise the compositions may include compounds of Formulas ID and IE, ID and IF, or ID, IE, and IF together.

In another aspect, the present technology provides complexes of the present compounds with transition metals (radioactive or non-radioactive). In any embodiments, the transition metal may be selected from Ga, Fe, Cu, Zn, Sc, Zn, Ti and the like, and their radioactive isotopes (e.g., $^{66/67/68}Ga$, $^{64}Cu$, $^{52}Fe$, and the like).

In another aspect the present technology provides methods of making the halogenated compounds herein. The methods are simple and are readily carried out in a single step in high yield, including high radio-yields, without the need for expensive purification techniques such as HPLC. In any embodiments, a non-halogenated precursor, such as a compound of Formula II (or a stereoisomer or salt thereof) is combined with a halogen source, e.g., an iodine source, bromine source or astatine source. As a non-limiting example, a compound of Formula II (or a stereoisomer or salt thereof) is combined with a compound an iodine source, including a source of radiolabeled iodine (e.g., $Na^{123}I$, $Na^{124}I$, $Na^{125}I$, or $Na^{131}I$), and an oxidant (e.g., chloramine T, or 1,3,4,6-tetrachloro-3α,6α-diphenyl glycoluril (iodogen), N-bromosuccinimide, N-chlorosuccinimide, etc.) to provide the mono- or bis-iodinated compound of Formula I, depending on the amount of iodine source. Radiolabled bromine and astatine sources may also be used, e.g., as disclosed herein. In any embodiments, the amount of radiolabeled bromine, iodine or astatine may range from, e.g., 0.1 mCi to 100 mCi or 1000 mCi, including from 0.5 or 1 mCi to any of 2 or 4 or 10 mCi. In any embodiments, the amount of radiolabeled bromine, iodine, or astatine may range from 1 to 4 mCi. The reaction mixture may be purified by passage through a plug or short column of $C_{18}$ or other suitable chromatographic material at room temperature and atmospheric pressure.

II

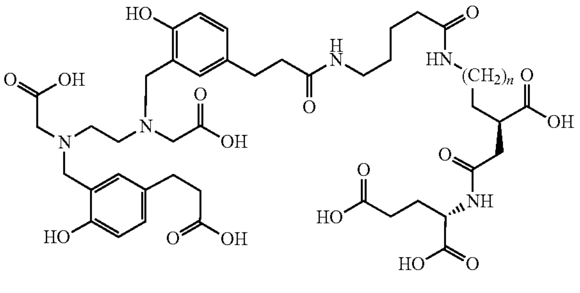

wherein n is 1, 2, 3, or 4.

In another aspect, the present technology provides a kit for preparing a compound of Formula I (including but not limited to a compound of Formula IA, IB, IC, ID, IE, IF). The kit may comprise a compound of Formula II and an oxidant sufficient to activate iodide, bromide or astatide for labeling of the compound of Formula II, a stereoisomer thereof, or a salt of the compound or stereoisomer. Thus, the kit may comprise separate packages of a compound of Formula II (e.g., where n=3, such as PSMA 11), an oxidant (e.g., chloramine T, or 1,3,4,6-tetrachloro-3α,6α-diphenyl glycoluril (iodogen), N-bromosuccinimide, N-chlorosuccinimide, etc.) and optionally dissolution reagents (e.g., acetic acid, NaOH, KOH), optionally quenching reagents (e.g., sodium sulfite, sodium thiosulfate, ascorbic acid, etc.), and optionally stabilizing reagents (e.g., ascorbic acid). Each reagent may be in solid form (e.g., lyophilized solid form) or in solution. Depending on the type of application (diagnostic vs therapeutic, single vs multiple doses) the weight of kit contents may vary in the range from 10 nmole to 100 μmoles to facilitate production of activities from 20-1000 mCi of the final product.

In another aspect the present technology provides a pharmaceutical composition comprising a pharmaceutical carrier or excipient and a compound as disclosed herein (including but not limited to a compound of any of Formulas I, IA, IB, IC, ID, IE, IF), or a composition as disclosed herein, or a complex as disclosed herein. In certain embodiments, the pharmaceutical carrier or excipient is or includes ascorbate. In any embodiments, the pharmaceutical composition includes an effective amount of the compound, composition or complex for imaging cancers associated with detectable PSMA expression in tumors or in the neovasculature supporting the tumors. Examples of such cancers include, but are not limited to, prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, or stomach cancer. In any embodiments of the pharmaceutical composition, the imaging is positron emission tomography (PET), single photon emission computed tomography (SPECT), planar imaging, PET/CT, SPECT/CT, multi-nuclide imaging, any other related imaging technique, or any combination or two or more thereof. In any embodiments, the pharmaceutical composition includes a therapeutically effective amount of the compound, composition or complex for treating cancers associated with detectable PSMA expression in tumors or in the neovasculature supporting the tumors. Examples of such cancers include, but are not limited to, prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, or stomach cancer.

In one aspect, the present disclosure provides a method for detecting solid tumors in a subject in need thereof comprising (a) administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA); and (b) detecting the presence of solid tumors in the subject by detecting radioactive levels emitted by the compound, composition or complex that are higher than a reference value. In some embodiments, the subject is human.

In another aspect, the present disclosure provides a method for selecting a subject for radiation therapy comprising (a) administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA); (b) detecting radioactive levels emitted by the compound, composition or complex; and (c) selecting the subject for radiation therapy when the radioactive levels emitted by the compound, composition or complex are higher than a reference value. In some embodiments, the subject is human.

In some embodiments of the methods disclosed herein, the radioactive levels emitted by the compound, composition or complex are detected using positron emission tomography (PET), single photon emission computed tomography (SPECT), planar imaging, PET/CT, SPECT/CT, multi-nuclide imaging, or any other related imaging technique. Additionally or alternatively, in some embodiments of the methods disclosed herein, the subject is diagnosed with, or is suspected of having a PSMA-expressing cancer (e.g., cancers associated with detectable PSMA expression in tumors or in the neovasculature supporting the tumors). Examples of PSMA-expressing cancers include, but are not limited to, prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer.

Additionally or alternatively, in some embodiments of the methods disclosed herein, the compound, composition or complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the compound, composition or complex is administered into the cerebral spinal fluid or blood of the subject.

In some embodiments of the methods disclosed herein, the radioactive levels emitted by the compound, composition or complex are detected between 1 to 168 hours after the compound, composition or complex is administered. In certain embodiments of the methods disclosed herein, the radioactive levels emitted by the compound, composition or complex are expressed as the percentage injected dose per gram tissue (% ID/g).

In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with cancer comprising administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA).

In another aspect, the present disclosure provides a method for treating cancer in a subject in need thereof comprising (a) administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA).

Additionally or alternatively, in some embodiments of the methods of the present technology, the compound, composition or complex is administered intravenously, intramuscularly, intraarterially, intrathecally, intracapsularly, intraorbitally, intradermally, intraperitoneally, transtracheally, subcutaneously, intracerebroventricularly, orally or intranasally.

In any and all embodiments disclosed herein, the methods of the present technology may comprise multiple cycles of administering any of the compounds, compositions or complexes disclosed herein (e.g., 1, 2, 3, 4, 5, 6, 7, 8, 9, 10 or more cycles).

The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11. In some embodiments, the cancer is associated with detectable PSMA expression in tumors or in the neovasculature supporting the tumors. Examples of such cancers include, but are not limited to, prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, and stomach cancer.

DETAILED DESCRIPTION

Figure 1:
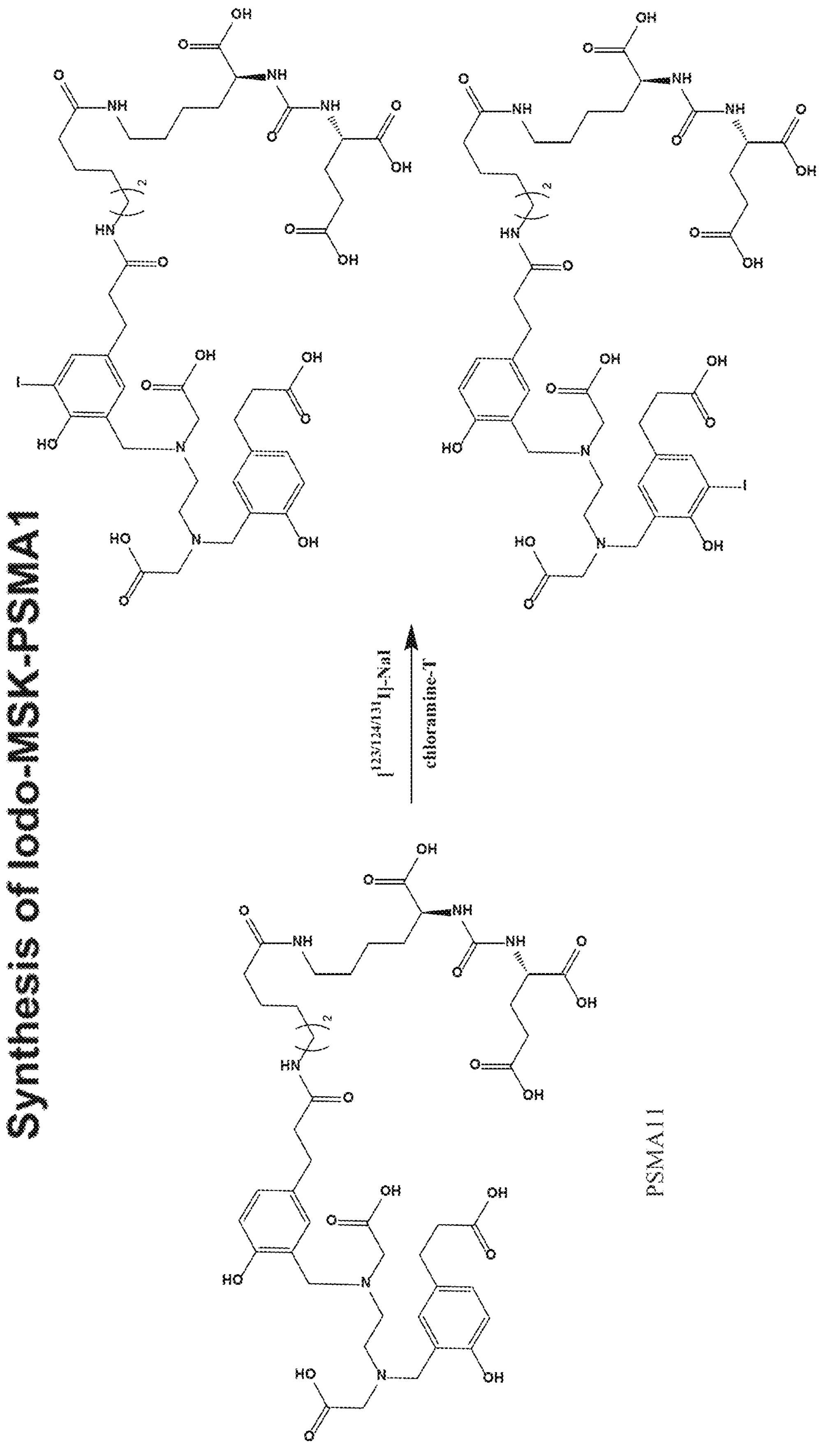
FIG. 1 shows an illustrative embodiment of a synthesis scheme for manufacturing radioiodinated PSMA targeting agents of the present technology (e.g., [I*]-MSK-PSMA1).

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR* 1: *A Practical Approach* (IRL Press at Oxford University Press); MacPherson et al. (1995) *PCR* 2: *A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Prostate Specific Membrane Antigen is highly overexpressed in both primary and metastatic prostate cancer and is therefore is a suitable target for development of novel radiopharmaceuticals (RPs). Iodine has several easily available isotopes that can be used for SPECT (I-123), PET (I-124) or therapy (I-131) with long half-life and therefore offers unique advantages. However, the currently available radioiodinated PSMA targeting RPs involve multiple steps for their production, thereby reducing their yields and posing significant challenges for producing therapeutic doses. To overcome these limitations, the present disclosure provides novel radiohalogenated (e.g., radioiodinated) PSMA targeting RPs (e.g., [I*]-MSK-PSMA1) that can be produced in quantitative yields in a single step from easily available chemical precursor DKFZ-PSMA11 (DP11).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

By "binding affinity" is meant the strength of the total noncovalent interactions between a single binding site of a molecule (e.g., a PSMA targeting agent) and its binding partner (e.g., PSMA). The affinity of a molecule X for its partner Y can generally be represented by the dissociation constant ($K_d$). Affinity can be measured by standard methods known in the art, including those described herein. A low-affinity complex contains a binding molecule that generally tends to dissociate readily from its target, whereas a high-affinity complex contains a binding molecule that generally tends to remain bound to its target for a longer duration.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" of a composition, is a quantity sufficient to achieve a desired prophylactic or therapeutic effect, e.g., an amount which results in the decrease in the symptoms associated with a disease that is being treated, e.g., the diseases or medical conditions associated with target polypeptide (e.g., prostate cancer etc.). The amount of a composition of the present technology administered to the subject will depend on the degree, type and severity of the disease and on the characteristics of the individual, such as general health, age, sex, body weight and tolerance to drugs. The skilled artisan will be able to determine appropriate dosages depending on these and other factors. The compositions of the present technology can also be administered in combination with one or more additional therapeutic compounds.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" refers to a molecule which recognizes and binds a target molecule, but does not substantially recognize and bind other molecules. The terms "specific binding," "specifically binds to," or is "specific for" a particular molecule (e.g., a PSMA targeting agent), as used herein, can be exhibited, for example, by a molecule having a $K_d$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M.

As used herein, the terms "subject," "individual," or "patient" are used interchangeably and refer to an individual organism, a vertebrate, a mammal, or a human. In certain embodiments, the individual, patient or subject is a human.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. By "treating a cancer" is meant that the symptoms associated with the cancer are, e.g., alleviated, reduced, cured, or placed in a state of remission.

It is also to be appreciated that the various modes of treatment of diseases as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

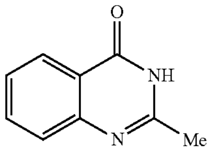

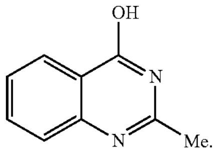

As another example, guanidines may exhibit the following isomeric forms in protic organic solution, also referred to as tautomers of each other:

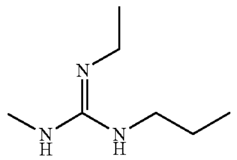

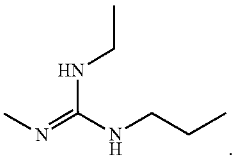

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Radiohalogenated PSMA Targeting Agents of the Present Technology

In one aspect, the present disclosure provides radiolabeled PSMA ligands, including radiohalogenated PSMA ligands such as radioiodinated PSMA ligands for imaging and radiation therapy. For example, there are provided compounds of Formula I, stereoisomers thereof, or pharmaceutically acceptable salts of the compounds or stereoisomers thereof:

I

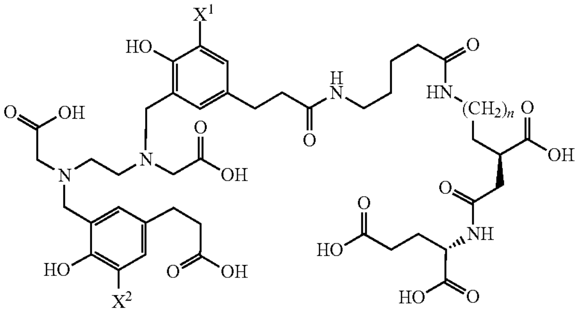

wherein, $X^1$ and $X^2$ are independently selected from the group consisting of H, I, Br, At, a radioisotope of Br (Br*), a radioisotope of I (I*), and a radioisotope of At (At*), provided at least one of $X^1$ and $X^2$ is not H; and n is 1, 2, 3, or 4.

In any embodiments, $X^1$ may be H. In any embodiments $X^2$ may be H. In any embodiments $X^1$ and $X^2$ may both be I (non-radiolabeled iodine) or a mixture of I and I*. In any embodiments, $X^1$ may be I, I* or a mixture thereof. In any embodiments, $X^2$ may be I, I* or a mixture thereof. In any embodiments $X^1$ and $X^2$ may both be Br (non-radiolabeled bromine) or a mixture of Br and Br*. In any embodiments, $X^1$ may be Br, Br* or a mixture thereof. In any embodiments, $X^2$ may be Br, Br* or a mixture thereof. In any embodiments $X^1$ and $X^2$ may both be At (non-radiolabeled astatine) or a mixture of At and At*. In any embodiments, $X^1$ may be At, At* or a mixture thereof. In any embodiments, $X^2$ may be At, At* or a mixture thereof.

In any embodiments, the compound of Formula I may be a compound of Formula IA, IB, or IC, a stereoisomer thereof, or a pharmaceutically acceptable salt of the compound or stereoisomer thereof:

IA

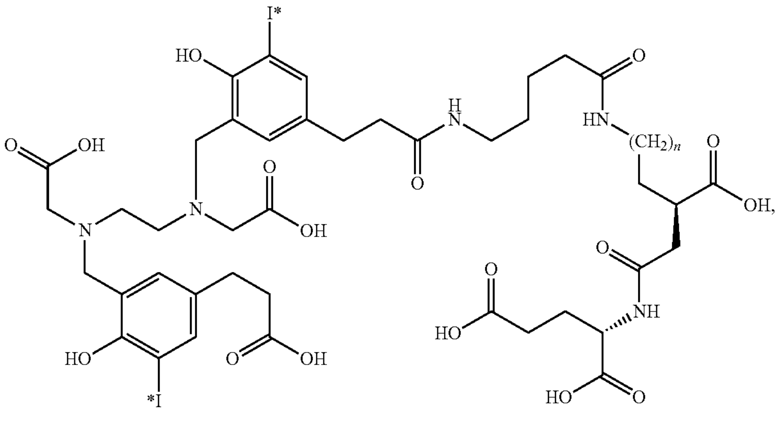

-continued

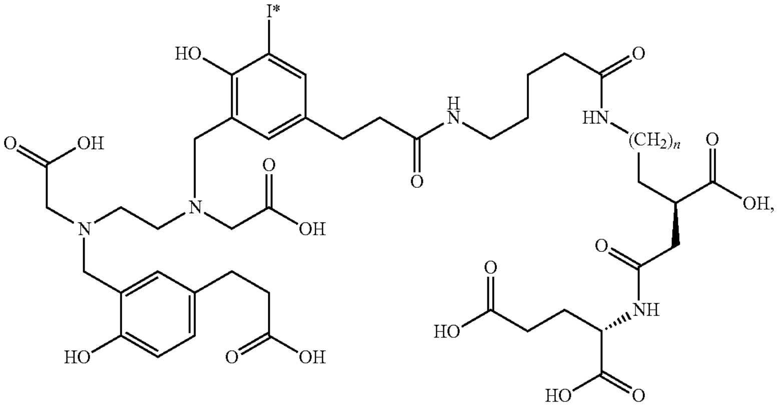

IB

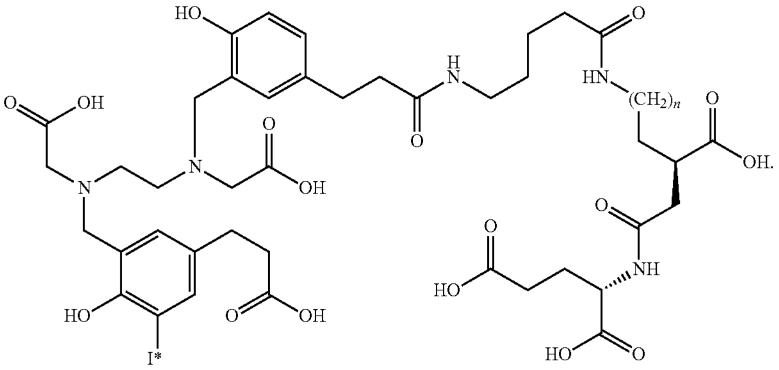

IC

In any embodiments of the compounds disclosed herein (including but not limited to compounds of Formulas I, IA, IB, and IC), n may be as noted above, 1, 2, 3, or 4. In any embodiments of the compounds herein n may be 3. Thus in certain embodiments, the compounds may be compounds of Formulas ID, IE or IF, stereoisomers thereof or pharmaceutically acceptable salts of the compounds or the isomers thereof:

ID

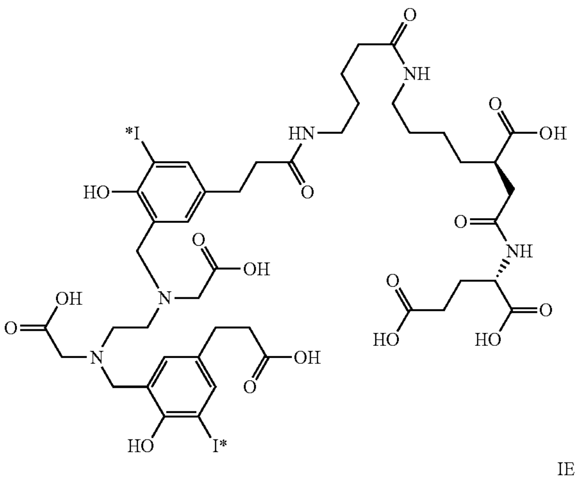

IE

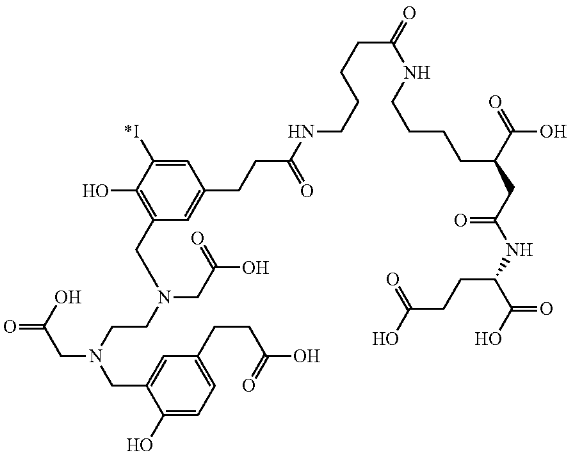

IF

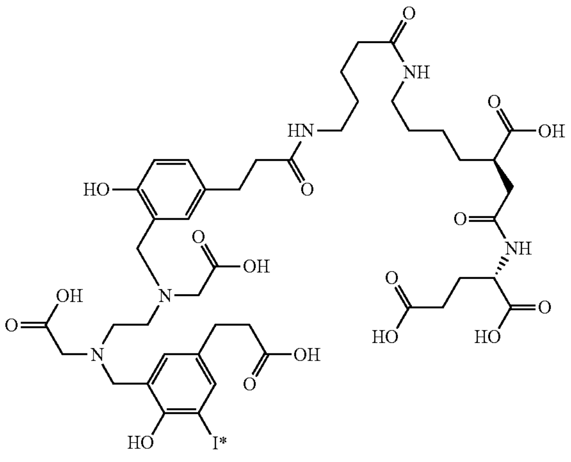

In any embodiments of compounds herein (including but not limited to compounds of Formulas I, IA, IB, IC, ID, IE, and IF), the radioisotope of I may be selected from $^{123}$I, $^{124}$I, $^{125}$I, or $^{131}$I. In any embodiments, the radioisotope of I may be $^{131}$I.

In another aspect, the present technology provides compositions including the compounds, e.g., compositions including any two or more compounds disclosed herein, such as, but not limited to compounds of Formulas I, IA, IB, IC, ID, IE, IF, and IE. As further non-limiting examples, the compositions may include compounds of Formulas IA and IB, IA and IC, or IA, IB and IC. Likewise the compositions may include compounds of Formulas ID and IE, ID and IF, or ID, IE, and IF together.

In another aspect, the present technology provides complexes of the present compounds with transition metals (radioactive or non-radioactive). In any embodiments, the transition metal may be selected from Ga, Fe, Cu, Zn, Sc, Zn, Ti, and the like, and their radioactive analogs (e.g., $^{66/67/68}$Ga, $^{64}$Cu, $^{52}$Fe, and the like).

In another aspect the present technology provides methods of making the radiohalogenated compounds herein. The methods are simple and are readily carried out in a single step in high yield, including high radio-yields, without the need for expensive purification techniques such as HPLC. In any embodiments, a non-iodinated precursor such as a compound of Formula II (or a stereoisomer or salt thereof) is combined with a bromine source, an iodine source, or an astatine source, including a source of radiolabeled bromine, iodine, or astatine (e.g., $Na^{76}Br$, $Na^{77}Br$, $Na^{82}Br$, $Na^{123}I$, $Na^{124}I$, $Na^{125}I$, $Na^{131}I$, or $Na^{211}At$), and an oxidant (e.g., chloramine T, or 1,3,4,6-tetrachloro-3a,6a-diphenyl glycoluril (iodogen), N-bromosuccinimide, N-chlorosuccinimide, etc.) to provide the mono- or bis-iodinated compound of Formula I, depending on the amount of iodine source. In any embodiment, the mixture of a source of radiolabeled bromine, iodine or astatine and oxidant may be combined or treated with an antioxidant (e.g., ascorbic acid) to stop production of the activated radiolabeled halide (e.g., $^{131}$ICl) and stabilize the solution after reaction with a compound of Formula II. In any embodiments, the amount of radiolabeled bromine, iodine or astatine may range from, e.g., 0.1 mCi to 100 mCi, or to 1000 mCi, including from 0.5 or 1 mCi to any of 2 or 4 or 10 mCi. In any embodiments, the amount of radiolabeled bromine, iodine or astatine may range from 1 to 4 mCi or 1 to 1000 mCi. The reaction mixture may be purified by passage through a plug or short column of $C_{18}$ or other suitable chromatographic material at room temperature and atmospheric pressure. The compound of Formula II is shown below:

II

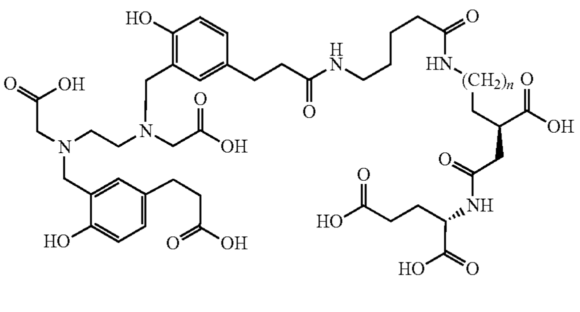

wherein n is 1, 2, 3, or 4.

In another aspect the present technology provides a pharmaceutical composition comprising a pharmaceutical carrier or excipient and a compound as disclosed herein (including but not limited to a compound of any of Formulas I, IA, IB, IC, ID, IE, IF), or a composition as disclosed herein, or a complex as disclosed herein. In certain embodiments, the pharmaceutical carrier or excipient is ascorbate. In any embodiments, the pharmaceutical composition includes an effective amount of the compound, composition or complex for imaging cancers associated with detectable PSMA expression in tumors or in the neovasculature supporting the tumors. Examples of such cancers include, but are not limited to, prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, or stomach cancer. In any embodiments of the pharmaceutical composition, the imaging is positron emission tomography (PET), single photon emission computed tomography, planar imaging, PET/CT, SPECT/CT, multi-nuclide imaging, or any other related imaging technique. In any embodiments, the pharmaceutical composition includes a therapeutically effective amount of the compound, composition or complex for treating cancers associated with detectable PSMA expression in tumors or in the neovasculature supporting the tumors. Examples of such cancers include, but are not limited to, prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, or stomach cancer.

Diagnostic and Therapeutic Methods of the Present Technology

In one aspect, the present disclosure provides a method for detecting solid tumors in a subject in need thereof comprising (a) administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA); and (b) detecting the presence of solid tumors in the subject by detecting radioactive levels emitted by the compound, composition or complex that are higher than a reference value. In some embodiments, the subject is human.

In another aspect, the present disclosure provides a method for selecting a subject for radiation therapy comprising (a) administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA); (b) detecting radioactive levels emitted by the compound, composition or complex; and (c) selecting the subject for radiation therapy when the radioactive levels emitted by the compound, composition or complex are higher than a reference value. In some embodiments, the subject is human.

In some embodiments of the methods disclosed herein, the radioactive levels emitted by the compound, composition or complex are detected using positron emission tomography, single photon emission computed tomography, planar imaging, PET/CT, SPECT/CT, multi-nuclide imaging, or any other related imaging technique. Additionally or alternatively, in some embodiments of the methods disclosed herein, the subject is diagnosed with, or is suspected of having a PSMA-expressing cancer (e.g., cancers associated with detectable PSMA expression in tumors or in the neovasculature supporting the tumors). Examples of PSMA-expressing cancers include, but are not limited to, prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, and stomach cancer.

Additionally or alternatively, in some embodiments of the methods disclosed herein, the compound, composition or complex is administered intravenously, intramuscularly, intraarterially, intrathecally, intracapsularly, intraorbitally, intradermally, intraperitoneally, transtracheally, subcutaneously, intracerebroventricularly, orally or intranasally. In certain embodiments, the compound, composition or complex is administered into the cerebral spinal fluid or blood of the subject.

In some embodiments of the methods disclosed herein, the radioactive levels emitted by the compound, composition or complex are detected between 1 to 168 hours after the compound, composition or complex is administered. In certain embodiments of the methods disclosed herein, the radioactive levels emitted by the compound, composition or complex are expressed as the percentage injected dose per gram tissue (% ID/g). The reference value may be calculated by measuring the radioactive levels present in non-tumor (normal) tissues, and computing the average radioactive levels present in non-tumor (normal) tissues ±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with cancer comprising administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA). In some embodiments, the subject is human. The compound, composition or complex is administered under conditions and for a period of time (e.g., according to a dosing regimen) sufficient for it to saturate PSMA(+) tumor cells. In some embodiments, the unbound compound, composition or complex is removed from the blood stream after administration of the compound, composition or complex.

In another aspect, the present disclosure provides a method for treating cancer in a subject in need thereof comprising (a) administering an effective amount of any compound, composition or complex described herein (e.g., a compound, composition or complex including Formulas I, IA, IB, IC, ID, IE, and IF) to the subject, wherein the compound, composition or complex is configured to localize to a solid tumor expressing prostate-specific membrane antigen (PSMA). In some embodiments, the subject is human. The compound, composition or complex is administered under conditions and for a period of time (e.g., according to a dosing regimen) sufficient for it to saturate PSMA(+) tumor cells. In some embodiments, the unbound compound, composition or complex is removed from the blood stream after administration of the compound, composition or complex. The therapeutic effectiveness of such a compound, composition, or complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Additionally or alternatively, in some embodiments of the methods of the present technology, the compound, composition or complex is administered intravenously, intramuscularly, intraarterially, intrathecally, intracapsularly, intraorbitally, intradermally, intraperitoneally, transtracheally, subcutaneously, intracerebroventricularly, orally or intranasally.

In any and all embodiments disclosed herein, the methods of the present technology may comprise multiple cycles of administering any of the compounds, compositions or complexes disclosed herein (e.g., 1, 2, 3, 4, 5, 6, 7, 8, 9, 10 or more cycles).

The methods for treating cancer may further comprise sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11. In some embodiments, the cancer is associated with detectable PSMA expression in tumors or in the neovasculature supporting the tumors. Examples of such cancers include, but are not limited to, prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, and stomach cancer.

Kits

In one aspect, the present technology provides a kit for preparing a compound of Formula I (including but not limited to a compound of Formula IA, IB, IC, ID, IE, IF). The kit may comprise separate packages of a compound of Formula II (e.g., PSMA 11), an oxidant (e.g., chloramine T, or 1,3,4,6-tetrachloro-3a,6a-diphenyl glycoluril (iodogen), N-bromosuccinimide, N-chlorosuccinimide, etc.), and optionally dissolution reagents (e.g., acetic acid, NaOH, KOH), optionally quenching reagents (e.g., sodium sulfite, sodium thiosulfate, ascorbic acid, etc.) and optionally stabilizing reagents (e.g., ascorbic acid). Each reagent may be in solid form (e.g., lyophilized solid form) or in solution.

Depending on the type of application (diagnostic vs therapeutic, single vs multiple doses) the weight of kit contents may vary in the range from 10 nmole to 100 μmoles to facilitate production of activities from 4-1000 mCi of the final product. The activities of the final product produced can be about 4 mCi, about 5 mCi, about 6 mCi, about 7 mCi, about 8 mCi, about 9 mCi, about 10 mCi, about 15 mCi, about 20 mCi, about 25 mCi, about 30 mCi, about 35 mCi, about 40 mCi, about 45 mCi, about 50 mCi, about 55 mCi, about 60 mCi, about 65 mCi, about 70 mCi, about 75 mCi, about 80 mCi, about 85 mCi, about 90 mCi, about 95 mCi, about 100 mCi, about 150 mCi, 200 mCi, about 250 mCi, 300 mCi, about 350 mCi, 400 mCi, about 450 mCi, 500 mCi, about 550 mCi, 600 mCi, about 650 mCi, 700 mCi, about 750 mCi, 800 mCi, about 850 mCi, 900 mCi, or about 1000 mCi. The activities of the final product produced can be in range of 4-20 mCi, 20-1000 mCi, 4-100 mCi, 100-200 mCi, 200-500 mCi, or 500-1000 mCi.

In another aspect, the kits comprise a compound, composition, or complex of Formula I (including but not limited to a compound of Formula IA, IB, IC, ID, IE, IF), and instructions for using the same to treat or diagnose a PSMA-expressing cancer in a patient.

The kits may further comprise a clearing agent. The compound, composition, or complex of Formula I (including but not limited to a compound of Formula IA, IB, IC, ID, IE, IF) may be provided in the form of a prefilled syringe or autoinjection pen containing a sterile, liquid formulation or lyophilized preparation of the compound.

If the kit components are not formulated for oral administration, a device capable of delivering the kit components through some other route may be included. Examples of such devices include syringes (for parenteral administration) or inhalation devices.

The kit components may be packaged together or separated into two or more containers. In some embodiments, the containers may be vials that contain sterile, lyophilized formulations of a compound, composition, or complex disclosed herein (e.g., a compound, composition or complex including Formulas I, IA, IB, IC, ID, IE, and IF) that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers.

EXAMPLES

Example 1

Synthesis of [I*]-MSK-PSMA1 (*=$^{123}$I, $^{124}$I, $^{125}$I, $^{131}$I, and the Like)

5-10 μL of the precursor PSMA11 (5-10 μg, MW 947, 5.3-10.6 nmoles) was added to an Eppendorf tube containing 1-4 mCi of [$^{131}$I]-NaI in 10-100 μL of 0.1N NaOH. To the resulting solution, 2 μL of chloramine-T solution (2 mg/mL in AcOH) was added. See FIG. 1. The mixture was vortexed and briefly centrifuged (20 s, 300 RPM) and allowed to react for 3 min. The product was diluted with 1 mL saline and loaded onto a C-18 cartridge (Strata™-X cartridge; 33 μm Polymeric Reversed Phase C-18, 30 mg/1 mL, #8B-S100-TAK, Phenomenex® Inc., Torrance, Calif. USA) that was preconditioned by passing 1 mL of 95% ethanol (USP for Injection) followed by 2.5 mL of pure water) and washed with 1 mL saline.

Figure 2:
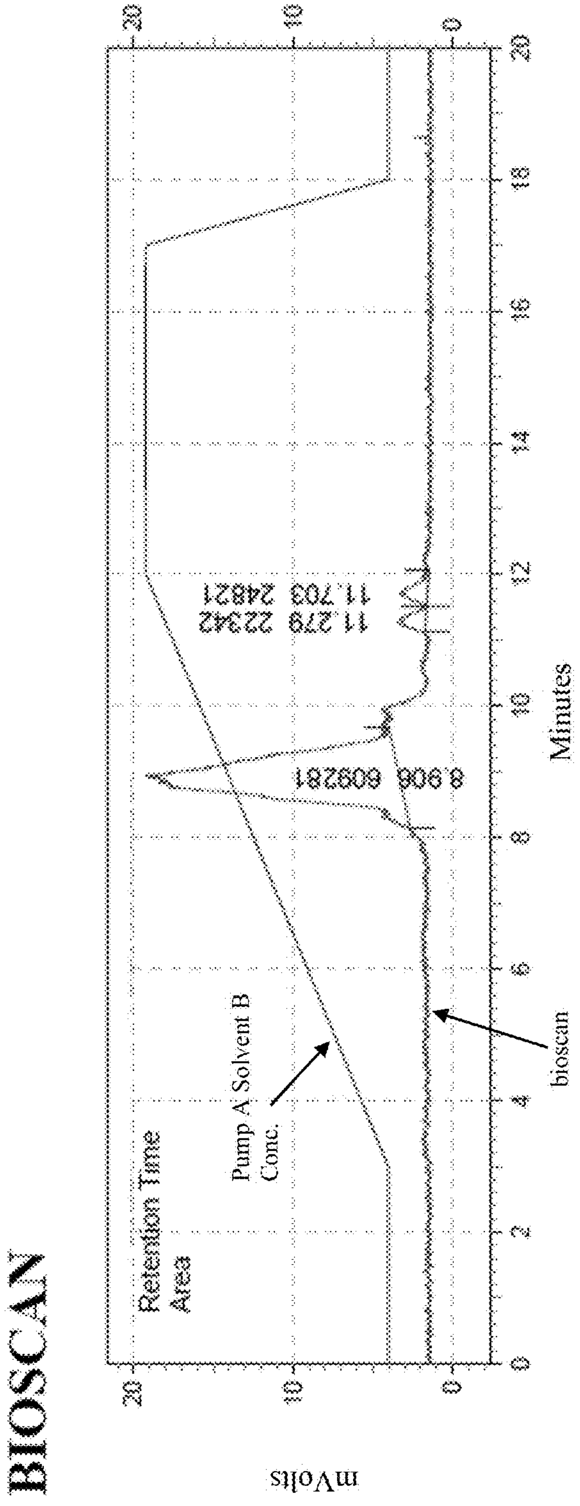
FIG. 2 shows a HPLC chromatogram of crude [$^{131}$I]-MSK-PSMA1.

FIG. 2 shows a HPLC chromatogram of crude [$^{131}$I]-MSK-PSMA1. The final pure product was eluted with 95% ethanol in saline in 100 μL fractions. The two fractions containing highest activity of the product (usually 2 and 3) were pooled, diluted in PBS and used for in vitro and in vivo studies. It is expected that other isotopes of iodine may be used the same way to prepare other radiolabeled compounds of Formula I.

Example 2

In Vitro and In Vivo Characterization of the Radiohalogenated (e.g., Radioiodinated) PSMA Targeting Agents of the Present Technology Saturation Binding Assay (SBA). Prostate cancer cell lines (LNCap (PSMA+) and PC3 (PSMA−)) were used to determine the affinity and number of binding sites of [$^{131}$I]-

MSK-PSMA1 and [$^{68}$Ga]DP11. About $10^6$ LNCap and PC3 cells were incubated with different concentrations (0.1-300 nM) of the radiolabeled PSMA-targeting agents for 1 hr. The cells were harvested and washed after incubation to remove unbound radiolabeled PSMA-targeting agent. The cells were counted for amount of bound radiolabeled PSMA-targeting agents using a gamma counter. The data obtained was analyzed by GraphPad Prism to determine Bmax and Kd of [$^{131}$I]-PSMA1 for both the cell lines.

PET imaging. Athymic nude mice were inoculated with PC3-PIP (PSMA+) prostate cancer cells and the xenografts were allowed to grow to 100-150 $mm^3$. [$^{131}$I]-MSK-PSMA1 and [$^{68}$Ga]DP11 were administered intravenously via tail vein and mice were imaged at 1, 4, 24, 48, 96 and 168 h after injection using PET. The images were later analyzed by AsiPro.

Biodistribution Studies. Athymic nude mice were inoculated with PC3-PIP (PSMA+) prostate cancer cells and the xenografts were allowed to grow to 100-150 $mm^3$. [$^{131}$I]-MSK-PSMA1 and [$^{68}$Ga]DP11 were administered intravenously. Mice were euthanized 1, 2, 6 and 24 h post injection and organs were collected, weighed and measured for radioactivity. The uptake of [$^{131}$I]-PSMA1 in each organ (represented as percentage injected dose per gram of organ (% ID/g)) was determined.

Autoradiography. LNCaP (PSMA+) tumor sections (10 mm) were incubated with [$^{131}$I]-MSK-PSMA-1 or [$^{131}$I]-MSK-PSMA-1 and excess PSMA-11 followed by washing. Sections were exposed to phosphorimaging plate for 24 h and scanned to detect binding of the radioactive probe to the PSMA expressed on the tumor cells.

Figure 3A:
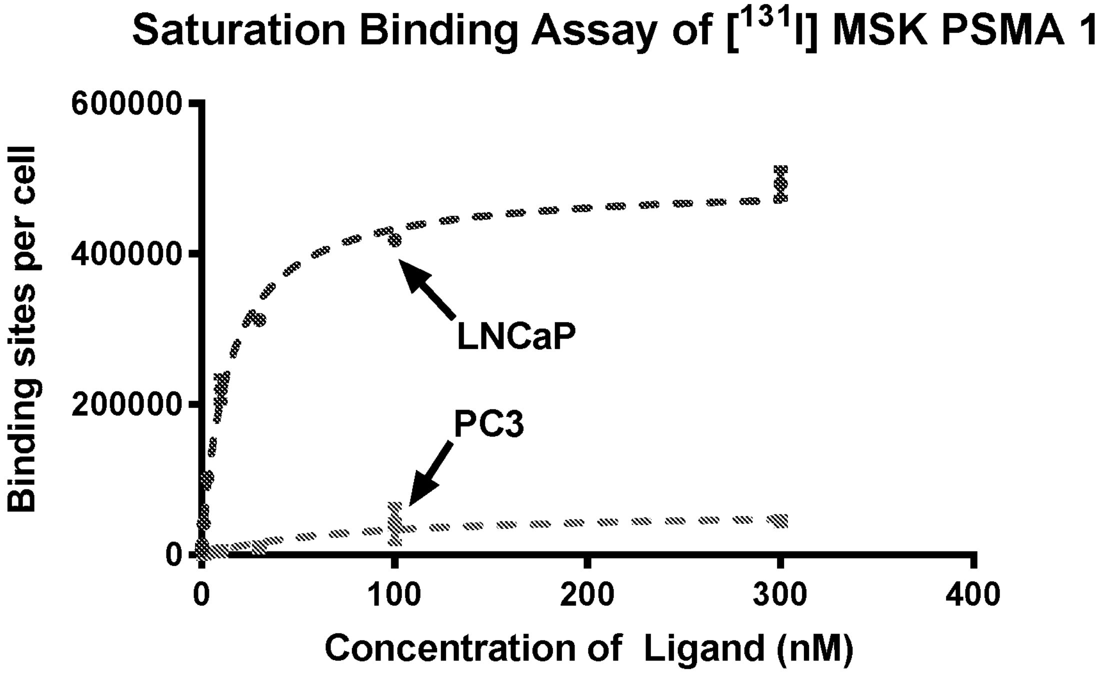
FIG. 3A and FIG. 3B show the in vitro saturation binding assay (SBA) results for [$^{131}$I]-MSK-PSMA1 and [$^{68}$Ga] DP11, respectively in LNCap (PSMA+) and PC3 (PSMA−) prostate cancer cell lines.
Figure 3B:
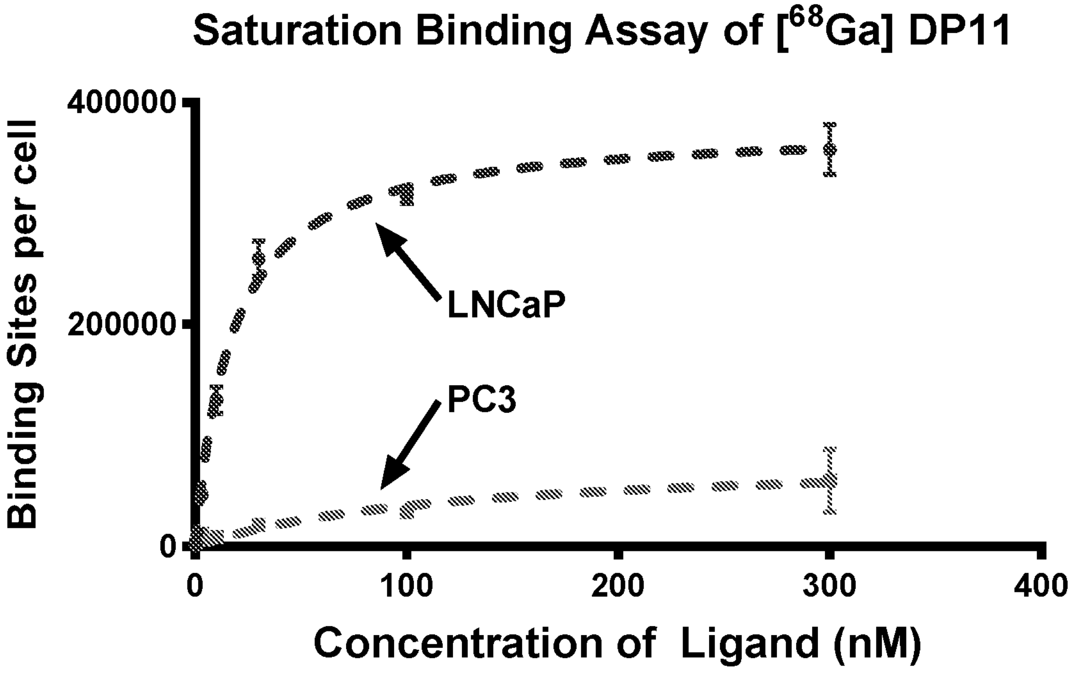
Figure 4A:
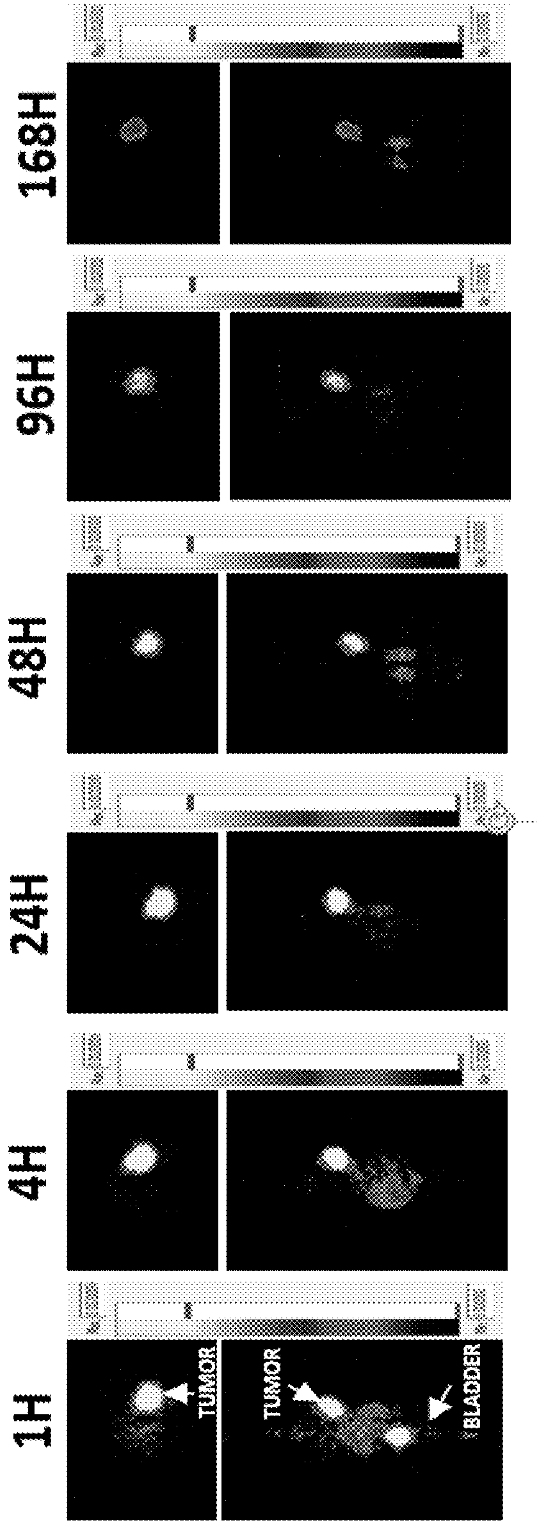
FIG. 4A and FIG. 4B show the in vivo positron emission tomography (PET) imaging results for [$^{131}$I]-MSK-PSMA1 and [$^{68}$GA]DP11, respectively, in PC3-PIP (PSMA+) (prostate cancer) xenograft mice.
Figure 4B:
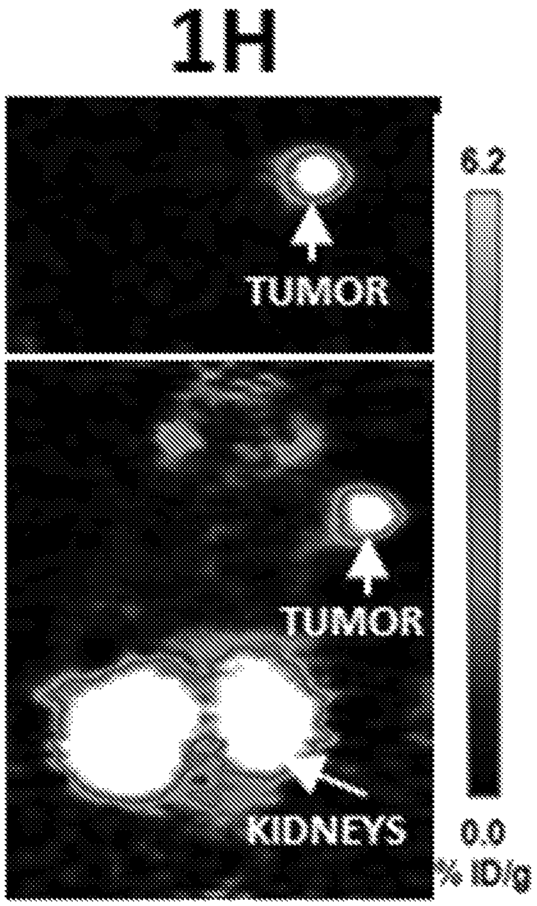
Figure 5A:
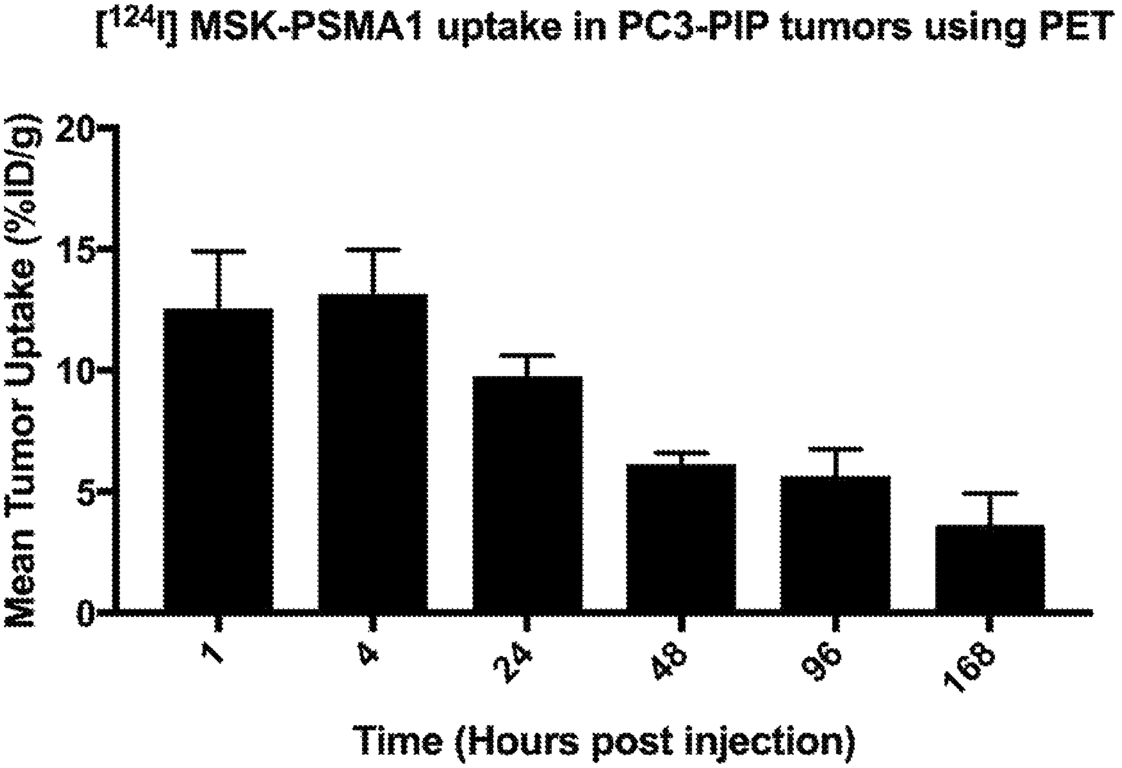
FIG. 5A shows tumor uptake results for [$^{124}$I] MSK-PSMA1 in PC3-PIP (prostate cancer) xenograft mice as determined by PET imaging.
Figure 5B:
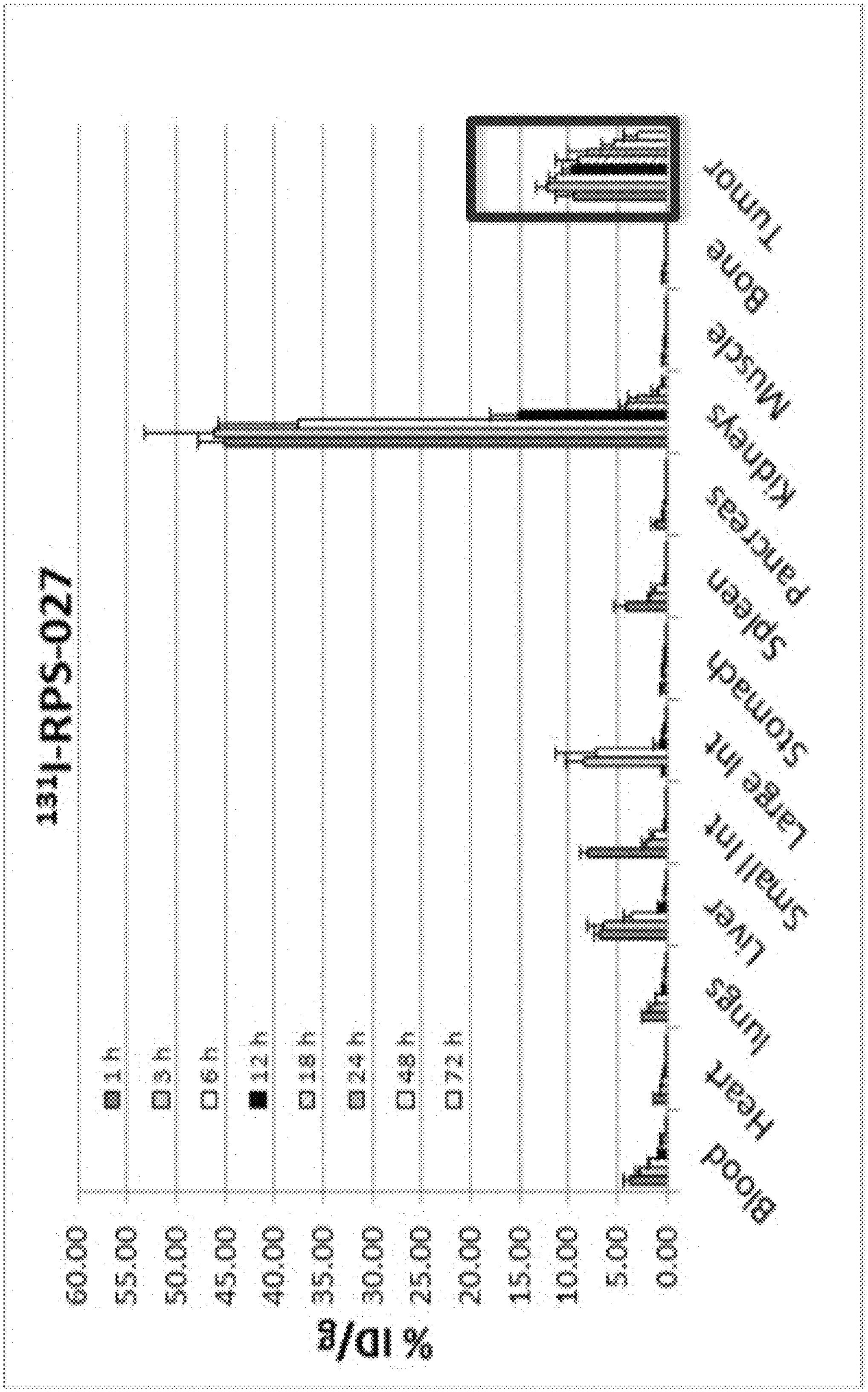
FIG. 5B shows biodistribution results for [$^{131}$I]-RPS-027 (advanced MIP-1095 analogue) in LNCap xenograft mice.

Results. [$^{124/131}$I]-MSK-PSMA1 was synthesized in >90% yields with specific activity >100 mCi/μmole. In vitro binding assays in LNCaP cells revealed specific binding with Bmax and Kd values of approximately 492999 sites per cell and 13.87 nM respectively in LnCap cells which are comparable to $^{68}$Ga labelled PSMA ligand in LNCaP cells. See FIGS. 3A-3B. PET imaging studies revealed significant tumor uptake of [$^{124}$I]-MSK-PSMA1 which was detectable up to 168 hours post injection with very minimal background, and was comparable to other conventional radiolabeled PSMA-targeting agents such as [$^{68}$Ga]DP11. See FIGS. 4A-4B and FIGS. 5A-5B. Uptake was also observed in the kidneys (which also expresses biological PSMA in mice) and bladder through which the unbound ligand was cleared rapidly than from tumor.

Figure 6A:
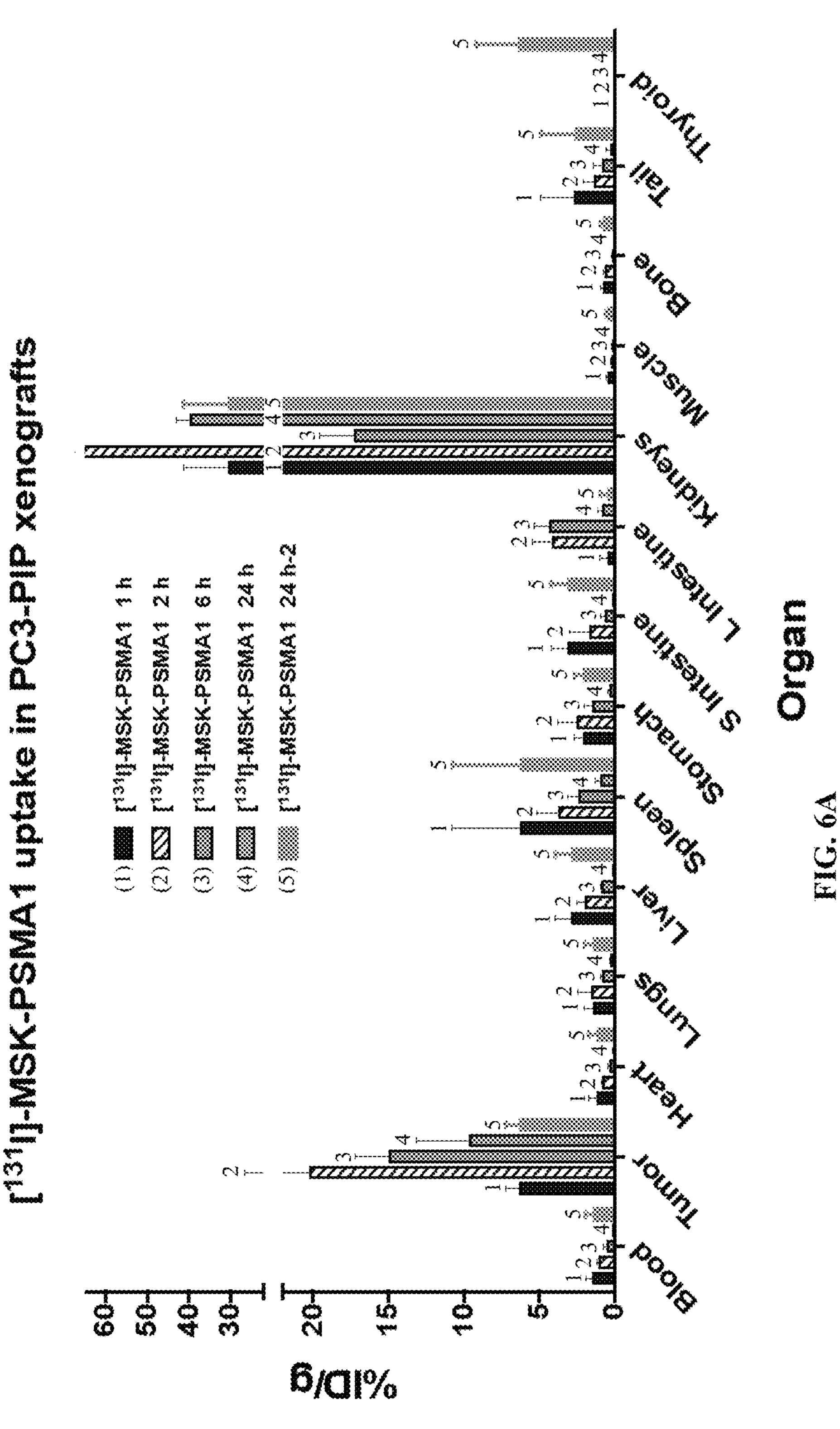
FIG. 6A and FIG. 6B show the in vivo biodistribution results for [$^{131}$I]-MSK-PSMA1 and [$^{68}$Ga]DP11 in prostate cancer xenograft mice.
Figure 6B:
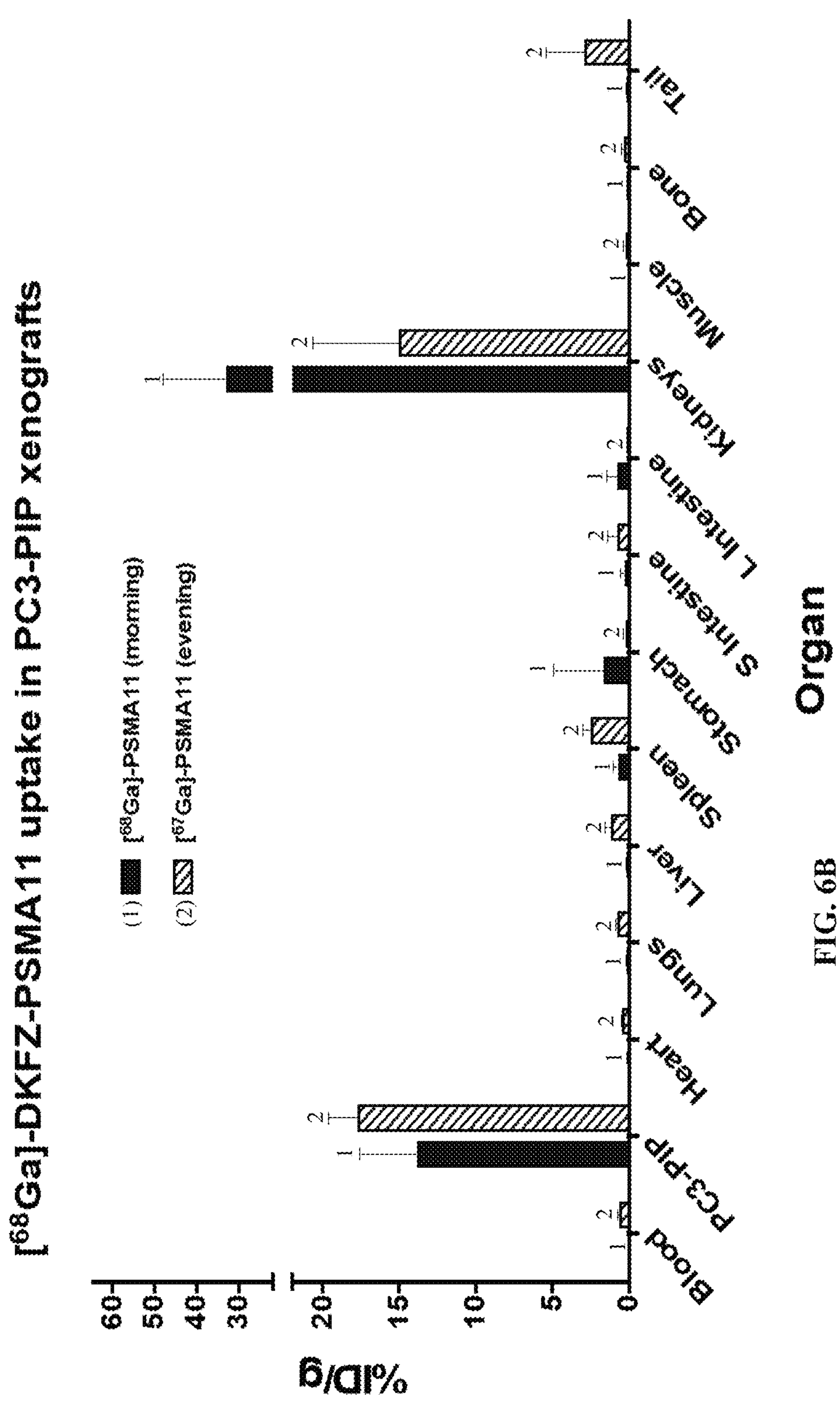

In vivo biodistribution studies in mice with PSMA positive PC3-PIP xenografts confirmed the PET imaging results, showing significant uptake in tumors, up to 7-20% ID/g at various time intervals, and kidneys, while rapidly cleared form rest of the body. See FIGS. 6A-6B. Biodistribution studies revealed tumor uptake of 6.3, 20.2, 15.0, and 9.7% ID/g at 1, 4, 6 and 24 h respectively.

Figure 8:
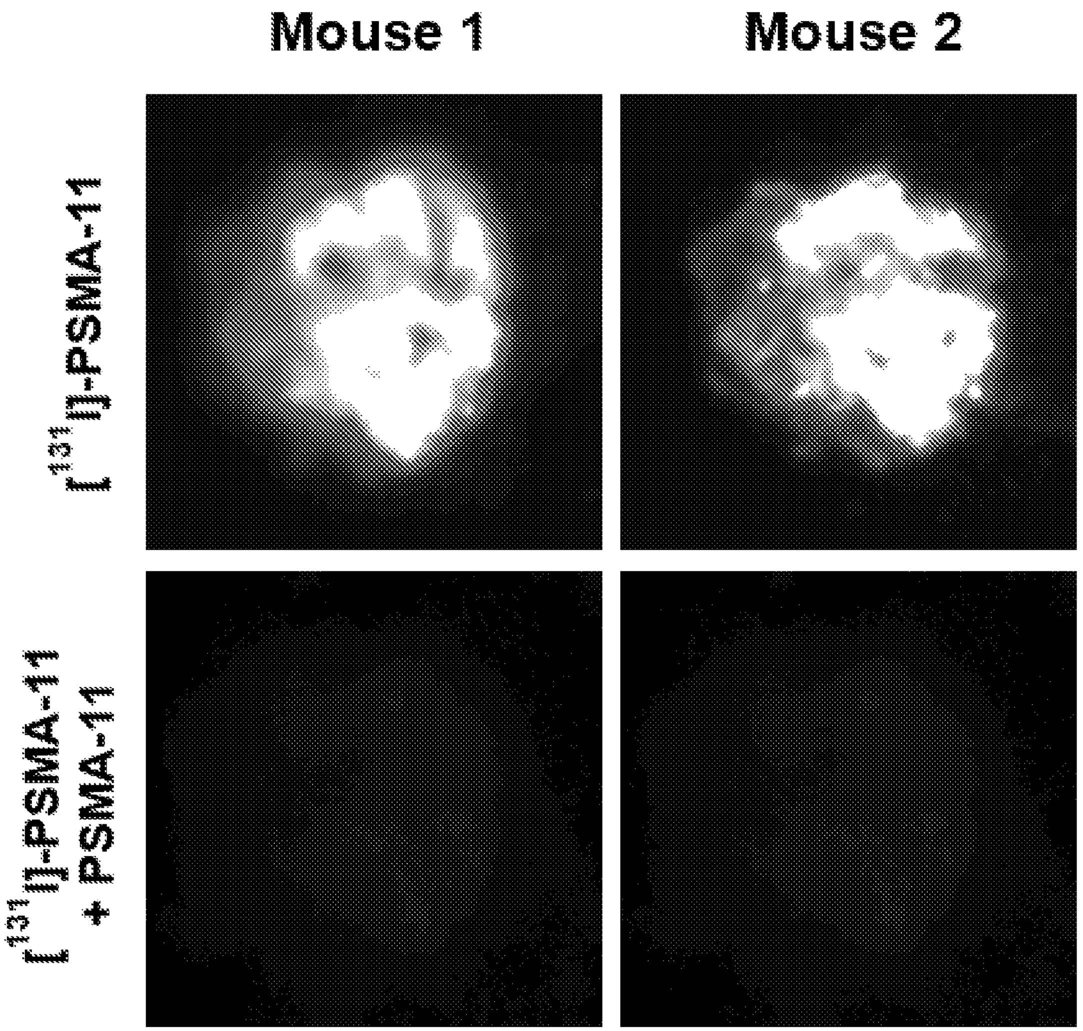
FIG. 8 shows in vitro autoradiography results that demonstrate the specificity of [$^{131}$I]-MSK-PSMA-1 to PSMA expressing tumor sections.

As shown in FIG. 8, [$^{131}$I]-MSK-PSMA-1 binds with high affinity to tumors that can be blocked by cold PSMA11, [$^{131}$I]-MSK-PSMA-1 is specific to PSMA expressed on the tumors.

These results demonstrate that the radiohalogenated (e.g., radioiodinated) PSMA targeting agents of the present technology are useful in methods for detecting solid tumors in a subject in need thereof.

Example 3

Therapeutic Effects of the Radiohalogenated (e.g., Radioiodinated) PSMA Targeting Agents of the Present Technology A cohort of athymic nude mice was inoculated with prostate specific membrane antigen (PSMA) expressing LNCaP-AR xenografts (5 million cells in 1:1 (media:matrigel) per xenograft). Tumor growth was monitored and the tumors were allowed to grow for 6 weeks to 300-500 $mm^3$. The cohort of mice was divided into 3 groups (n=6). Group 1 corresponded to the untreated control mice. Group 2 was treated with 20 mCi/kg×3 of [$^{131}$I]-MSK-PSMA1, 1 time every week for 3 weeks. Group 3 was treated with 40mCi/kg×3 of [$^{131}$I]-MSK-PSMA1, 1 time every week for 3 weeks. Before each treatment the mice were i.p. injected with 100 μL of 1% KI solution to block the thyroid uptake of any free [$^{131}$I]-Iodide resulting from metabolism of the tracer in vivo. Response to each treatment was determined by measuring the tumor size twice a week. The results were plotted as tumor volume with respect to time (days) post beginning of the treatment.

Figure 7:
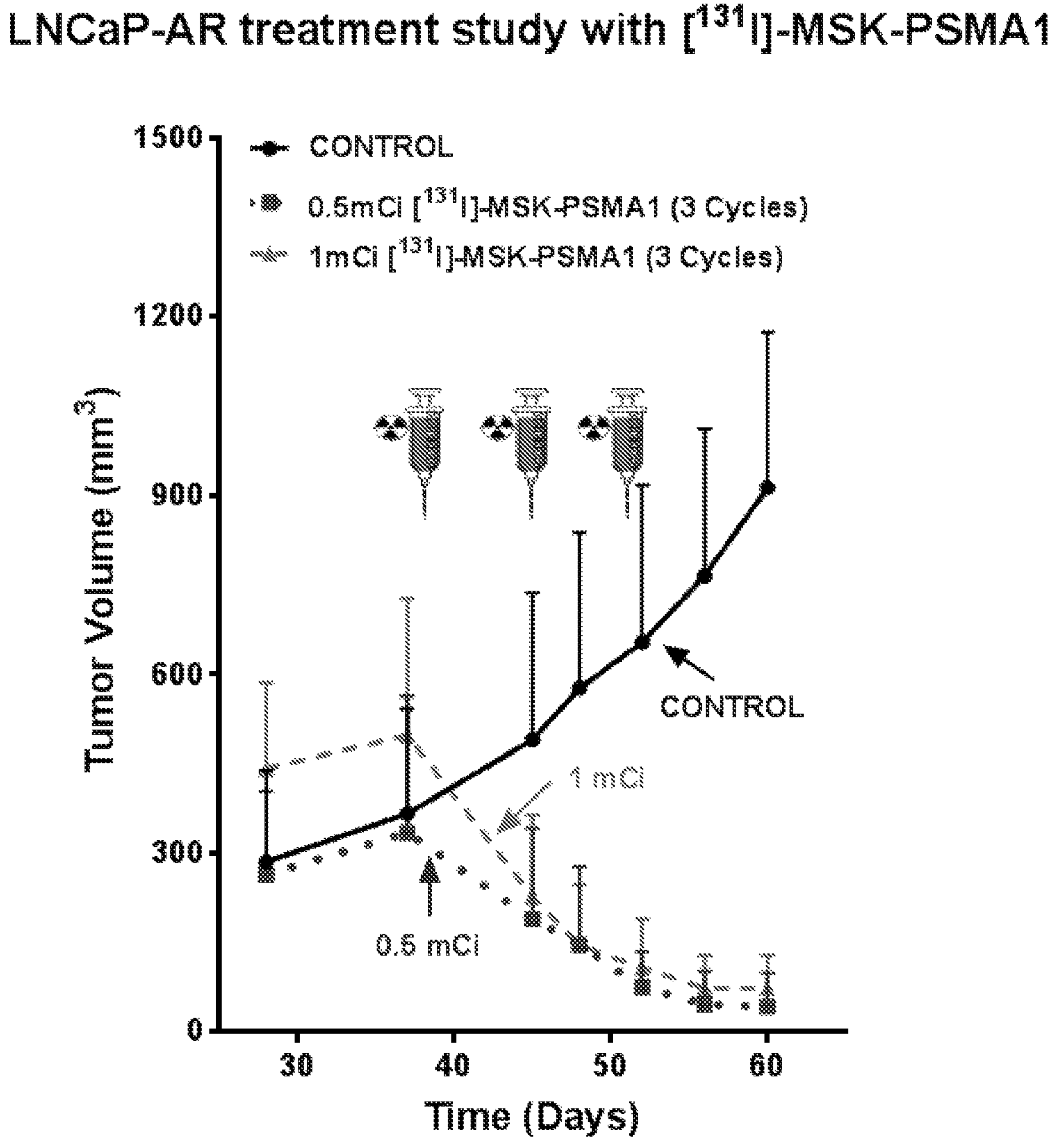
FIG. 7 shows the therapeutic effects of [$^{131}$I]-MSK-PSMA1 in LNCaP-AR xenograft mice.

As shown in FIG. 7, LNCaP-AR xenograft animals treated with 0.5 mCi and 1 mCi of [$^{131}$I]-MSK-PSMA1 showed a significant reduction in tumor volume over time compared to untreated control xenograft animals.

These results demonstrate that the radiohalogenated (e.g., radioiodinated) PSMA targeting agents of the present technology are useful in methods for treating PSMA-expressing cancer in a subject in need thereof.

Example 4

Kit formulation for the Synthesis of [I*]-MSK-PSMA1 (*=$^{123}$I, $^{124}$I, $^{125}$I, $^{131}$I, and the Like)

The present technology includes kit type formulation to facilitate on-site synthesis of [I*]-MSK-PSMA1. The kit formulation will contain following sterile vials: 1) pre-weighed amount of the precursor PSMA11 and a stabilizer (if necessary) in lyophylized or solution form; 2) oxidant such as chloramine-T or iodogen lyophylized or in solution form and 3) reagents/solvents for dissolution and quenching. The precursor and reagents will be dissolved in appropriate solvents and added to vial containing the precursor PSMA11. To this vial, a radioactive solution of pure [I]-NaI solution in dilute NaOH (0.01-0.1 N NaOH) will be added and allowed to react for 2-5 min. If necessary, the mixture will be quenched with a suitable quencher such as sodium thiosulfate. This crude mixture will be passed through a C-18 Sep-Pak or similar cartridge and washed with 1-3 mL saline. The product will be elute in 300-500 μL of Ethanol and diluted in saline and used for imaging or therapy applications.

Example 5

Therapeutic Effects of the Radiohalogenated (e.g., Radioiodinated) PSMA Targeting Agents of the Present Technology A cohort of athymic nude mice will be inoculated with prostate specific membrane antigen (PSMA) expressing LNCaP-AR cells (5 million cells in 50:50 media:matrigel). The tumor growth will be monitored and will be permitted to reach an average size of 200 $mm^3$ in 6 weeks. The cohort of mice will be divided into multiple groups (n≥5); group 1 will be the untreated control group; group 2 mice will be administered a single dose of 20 mCi/kg of [$^{131}$]I-MSK-PSMA1; group 3 will be administered 10 mCi/kg×2 of [$^{131}$I]-MSK-PSMA1, 2 times every 2 weeks; and group 4 will be administered 7 mCi/kg×3 of [$^{131}$I]-MSK-PSMA1, 3 times every 2 weeks. Before each treatment the mice will be i.p. injected with 100 μL of 1% KI solution to block the thyroid uptake of any free [$^{131}$I]-Iodide resulting from metabolism of the tracer in vivo. Response to the treatment as demonstrated by tumor regression will be monitored by measuring the size of the tumor 2 times every week. The results will be plotted as tumor volume changes with respect to time (days) post beginning of the treatment.

It is anticipated that LNCaP-AR xenograft animals treated with the various doses of [$^{131}$I]-MSK-PSMA1 will exhibit a significant reduction in tumor volume over time compared to untreated control xenograft animals.

These results demonstrate that the radiohalogenated (e.g., radioiodinated) PSMA targeting agents of the present technology are useful in methods for treating PSMA-expressing cancer in a subject in need thereof.

Example 6

Clinical Production Method and Stabilizing Agent Formulation (Suitable for Kits) to Minimize Radiolysis Four μL of chloramine-T solution in acetic acid (20 μg) was added to 2 mL of 0.9% sodium chloride and transferred to a glass vial containing PSMA11 (100 μg). To the resulting solution, 0.4 mL [$^{131}$I]-NaI solution (41 mCi) in 0.1 N NaOH was added and allowed to react for 3 min. Two ml of ascorbic acid solution in water (5 μg/mL) was added to the reaction vial to stop the reaction and the product was transferred via 0.22 micron yellow filter to a 50 ml final product vial containing 17 mL ascorbate (5 μg/mL) and the purity and stability of the product was measured. The yield of the product was >95% as determined by analytical HPLC.

Figure 9A:
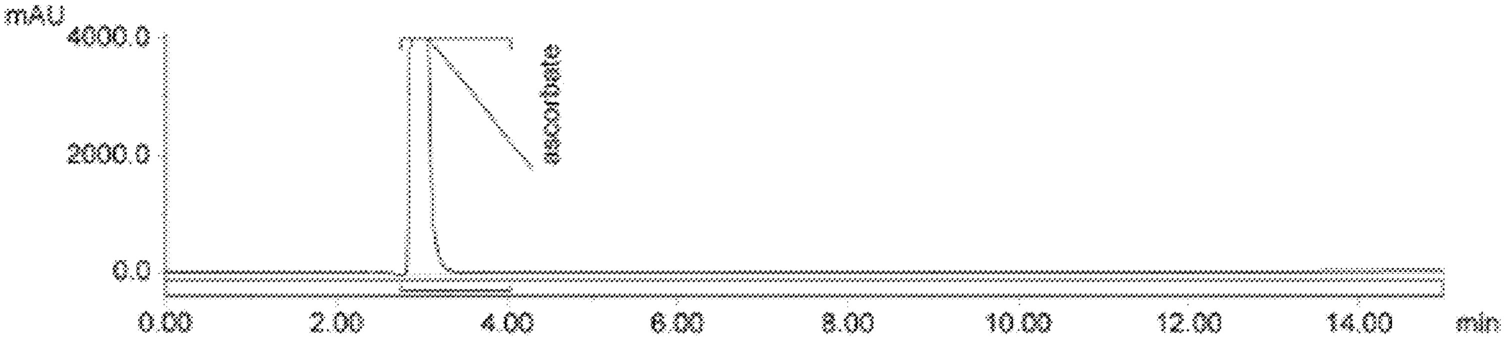
FIGS. 9A-9B show an exemplary analytical HPLC profile of [$^{131}$I]-I-MSK-PSMA1 at end of the synthesis in Ascorbate formulation.
Figure 9B:
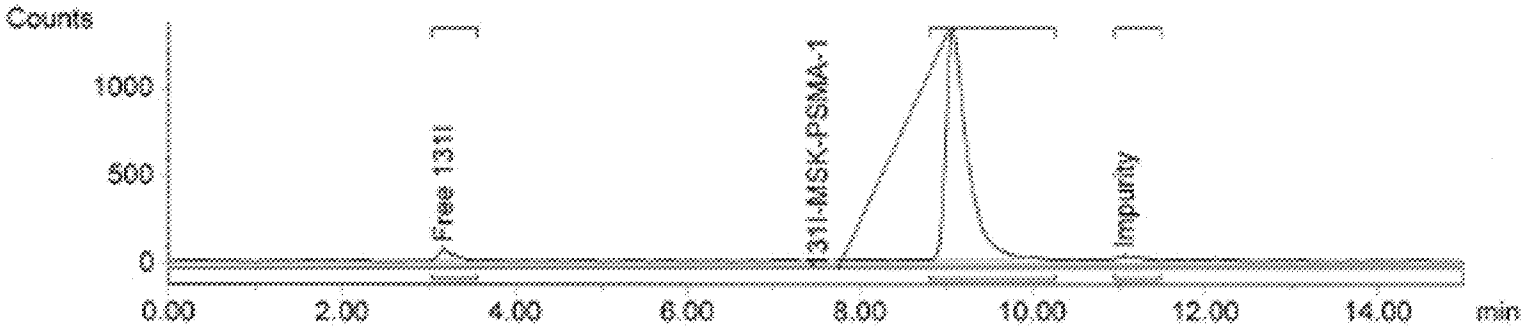
Figure 10A:
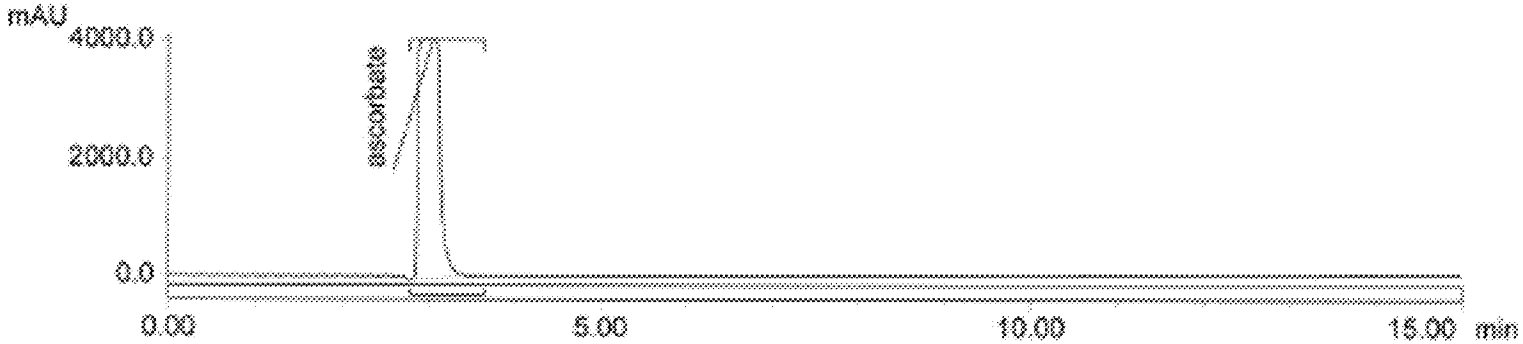
FIGS. 10A-10B show an exemplary analytical HPLC profile of [$^{131}$I]-I-MSK-PSMA1 at 18 h post formulation in Ascorbate solution.
Figure 10B:
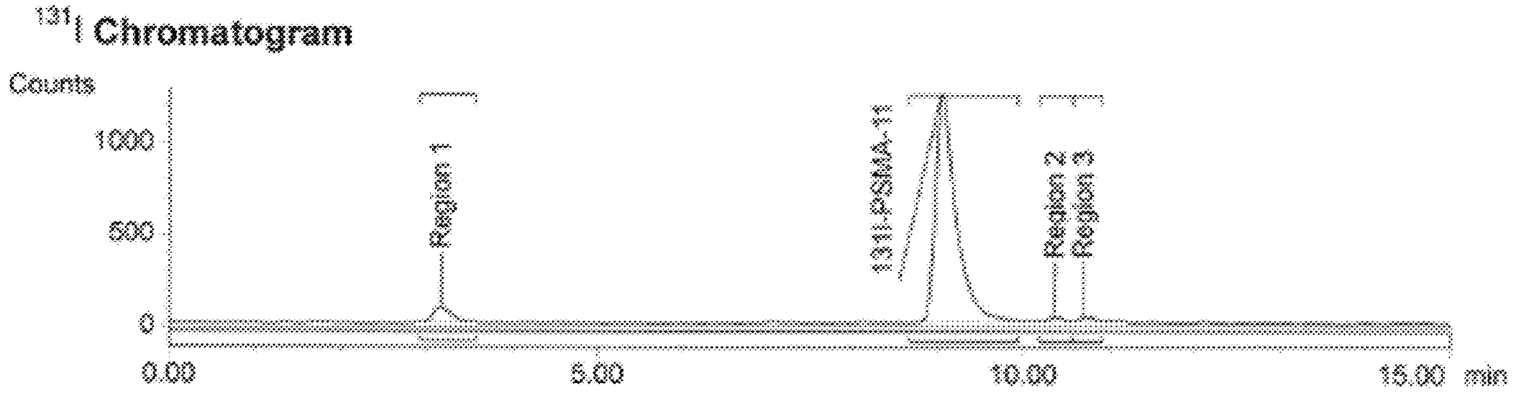
Figure 11A:
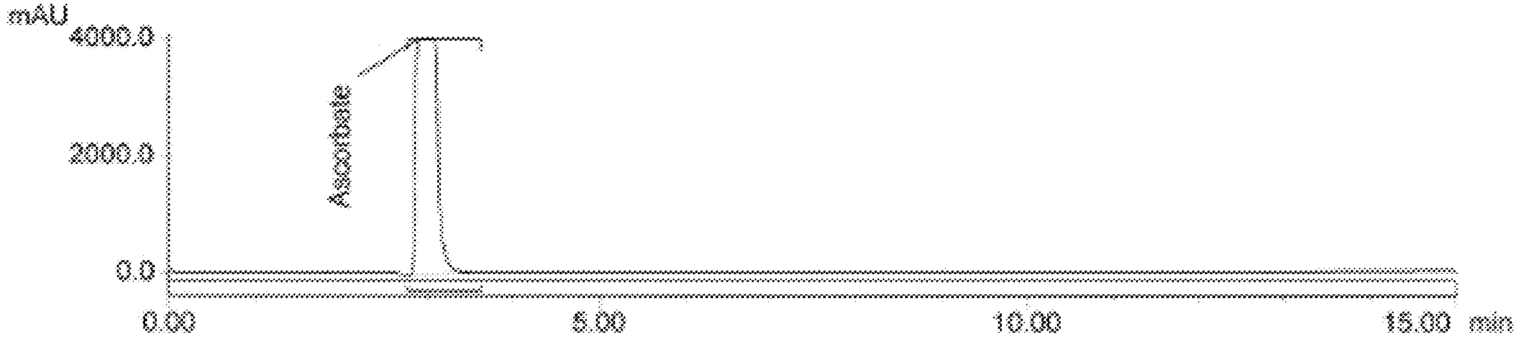
FIGS. 11A-11B show an exemplary analytical HPLC profile of [$^{131}$I]-I-MSK-PSMA1 at 45 h post formulation in Ascorbate solution.
Figure 11B:
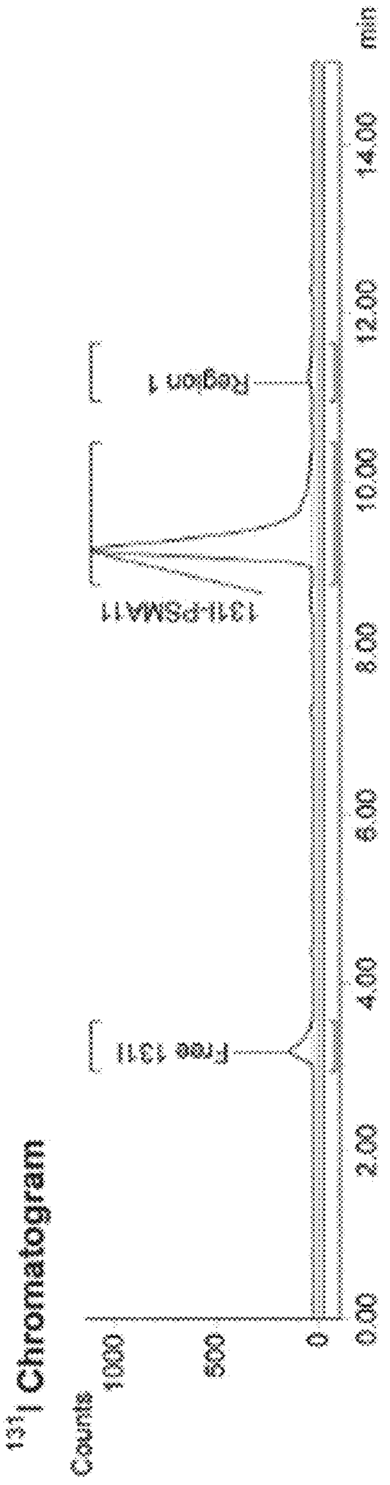

As shown in FIGS. 10A-10B, and 11A-11B, [$^{131}$I]-I-MSK-PSMA1 showed minimal degradation at 18 hours and 45 hours post formulation in Ascorbate solution. Compare FIGS. 10A-10B, and 11A-11B against FIGS. 9A-9B.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

Exemplary Embodiment 1: A compound of Formula I, a stereoisomer thereof, or a pharmaceutically acceptable salt of the compound or stereoisomer thereof:

I

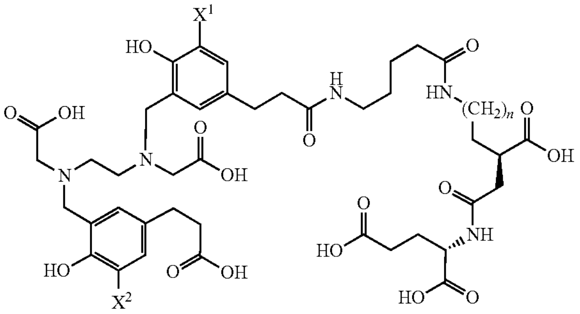

wherein, $X^1$ and $X^2$ are independently selected from the group consisting of H, I, Br, At, a radioisotope of Br (Br*), a radioisotope of I (I*), and a radioisotope of At (At*), provided at least one of $X^1$ and $X^2$ is not H; and n is 1, 2, 3, or 4.

Exemplary Embodiment 2: The compound of Embodiment 1, wherein the radioisotope of Br*, I* and At* is selected from $^{76}$Br, $^{77}$Br, $^{82}$Br, $^{123}$I, $^{124}$I, $^{125}$I, $^{131}$I, or $^{211}$At.

Exemplary Embodiment 3: The compound of Embodiment 1, wherein the radioisotope of I* is selected from $^{131}$I.

Exemplary Embodiment 4: The compound of any one of Embodiments 1-3, wherein both $X^1$ and $X^2$ are a radioisotope of iodine.

Exemplary Embodiment 5: The compound of any one of Embodiments 1-3, wherein $X^1$ is I* and $X^2$ is H or $X^1$ is H and $X^2$ is I*.

Exemplary Embodiment 6: The compound of any one of Embodiments 1-5, wherein n is 3.

Exemplary Embodiment 7: The compound of Embodiment 1 having Formula IA, IB, or IC, a stereoisomer thereof, or a pharmaceutically acceptable salt of the compound or stereoisomer thereof:

IA

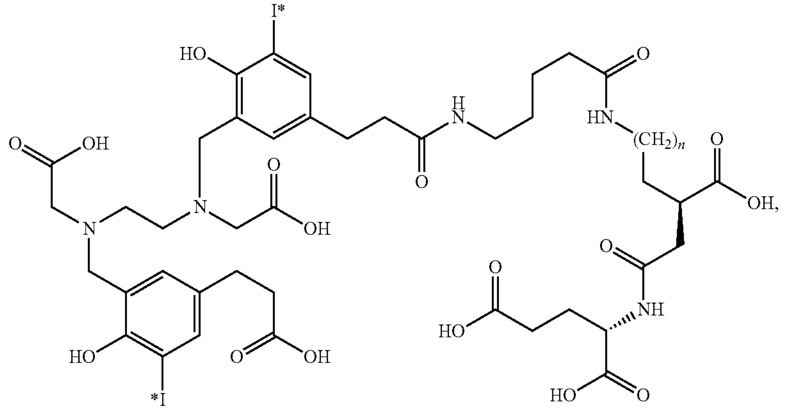

IB

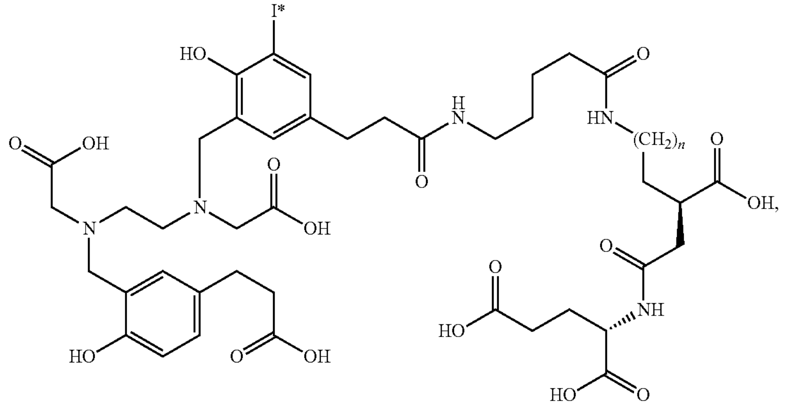

IC

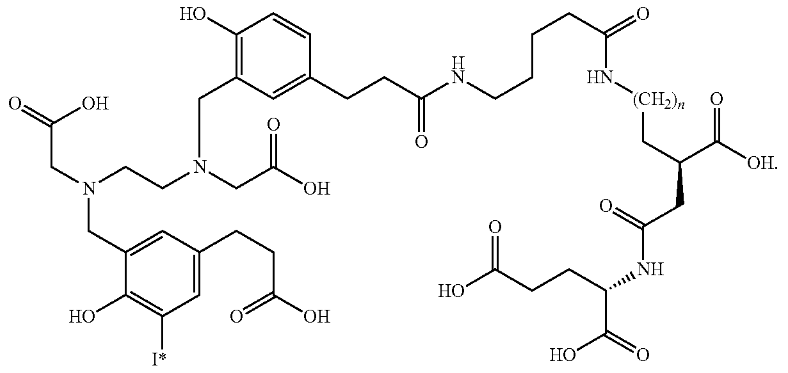

Exemplary Embodiment 8: A composition comprising two or more compounds of any one of Embodiments 1-7.

Exemplary Embodiment 9: A complex comprising a compound of any one of Embodiments 1-7 and a transition metal.

Exemplary Embodiment 10: The complex of Embodiment 9, wherein the transition metal is selected from Ga, Fe, Cu, Zn, Sc, Zn, Ti, or a radioisotope thereof.

Exemplary Embodiment 11: A pharmaceutical composition comprising a pharmaceutical carrier or excipient and a compound of any one of Embodiments 1-7, the composition of Embodiment 8, or the complex of Embodiments 9 or 10.

Exemplary Embodiment 12: The pharmaceutical composition of Embodiment 11 comprising an effective amount of the compound, composition or complex for imaging a cancer associated with detectable PSMA expression in tumors or tumor neovasculature.

Exemplary Embodiment 13: The pharmaceutical composition of Embodiment 12, wherein the cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer.

Exemplary Embodiment 14: The pharmaceutical composition of any one of Embodiments 11-13, wherein the imaging is Positron emission tomography (PET), single-photon emission computerized tomography (SPECT), planar imaging, PET/CT, SPECT/CT, multi-nuclide imaging, or any combination thereof.

Exemplary Embodiment 15: The pharmaceutical composition of any one of Embodiments 11-14 comprising a therapeutically effective amount of the compound, composition or complex for treating a cancer associated with detectable PSMA expression in tumors or tumor neovasculature.

Exemplary Embodiment 16: The pharmaceutical composition of Embodiment 15, wherein the cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer.

Exemplary Embodiment 17: A kit comprising a compound of Formula II and an oxidant sufficient to activate iodide, bromide or astatide for labeling of the compound of Formula II, a stereoisomer thereof, or a salt of the compound or stereoisomer:

II

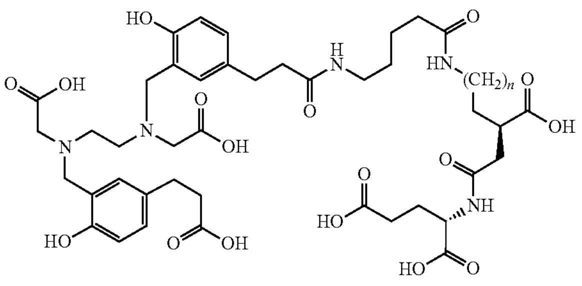

wherein n is 1, 2, 3, or 4.

Exemplary Embodiment 18: The kit of Embodiment 17 wherein n is 3 and the compound of Formula II is PSMA 11.

Exemplary Embodiment 19: The kit of Embodiment 17 or Embodiment 18 wherein the oxidant is chloramine T or 1,3,4,6-tetrachloro-3a,6a-diphenyl glycoluril.

Exemplary Embodiment 20: A method for detecting solid tumors in a subject in need thereof comprising (a) administering an effective amount of the pharmaceutical composition of any one of Embodiments 11-16 to the subject, wherein the compound, composition or complex is configured to localize to a solid tumor expressing prostate-specific membrane antigen (PSMA); and (b) detecting the presence of solid tumors in the subject by detecting radioactive levels emitted by the pharmaceutical composition that are higher than a reference value.

Exemplary Embodiment 21: A method for selecting a subject for radiation therapy comprising (a) administering an effective amount of the pharmaceutical composition of any one of Embodiments 11-16 to the subject, wherein the compound, composition or complex is configured to localize to a solid tumor expressing prostate-specific membrane antigen (PSMA); (b) detecting radioactive levels emitted by the pharmaceutical composition; and (c) selecting the subject for radiation therapy when the radioactive levels emitted by the pharmaceutical composition are higher than a reference value.

Exemplary Embodiment 22: The method of Embodiment 20 or 21, wherein the radioactive levels emitted by the pharmaceutical composition are detected using positron emission tomography, single photon emission computed tomography, planar imaging, PET/CT, SPECT/CT, multinuclide imaging, or any combination thereof.

Exemplary Embodiment 23: The method of any one of Embodiments 20-22, wherein the subject is diagnosed with, or is suspected of having a PSMA-expressing cancer.

Exemplary Embodiment 24: The method of Embodiment 23, wherein the PSMA-expressing cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer.

Exemplary Embodiment 25: The method of any one of Embodiments 20-24, wherein the pharmaceutical composition is administered into the cerebral spinal fluid or blood of the subject.

Exemplary Embodiment 26: The method of any one of Embodiments 20-25, wherein the pharmaceutical composition is administered intravenously, intramuscularly, intraarterially, intrathecally, intracapsularly, intraorbitally, intradermally, intraperitoneally, transtracheally, subcutaneously, intracerebroventricularly, orally or intranasally.

Exemplary Embodiment 27: The method of any one of Embodiments 20-26, wherein the radioactive levels emitted by the pharmaceutical composition are detected between 1 to 168 hours after the pharmaceutical composition is administered.

Exemplary Embodiment 28: The method of any one of Embodiments 20-27, wherein the radioactive levels emitted by the pharmaceutical composition are expressed as the percentage injected dose per gram tissue (% ID/g).

Exemplary Embodiment 29: The method of any one of Embodiments 20-28, wherein the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Exemplary Embodiment 30: A method for increasing tumor sensitivity to radiation therapy in a subject diagnosed with cancer comprising administering an effective amount of the pharmaceutical composition of any one of Embodiments 11-16 to the subject, wherein the compound, composition or complex is configured to localize to a solid tumor expressing prostate-specific membrane antigen (PSMA).

Exemplary Embodiment 31: A method for treating cancer in a subject in need thereof comprising administering an effective amount of the pharmaceutical composition of any one of Embodiments 11-16 to the subject, wherein the compound, composition or complex is configured to localize to a solid tumor expressing prostate-specific membrane antigen (PSMA).

Exemplary Embodiment 32: The method of any one of Embodiments 30-31, wherein the pharmaceutical composition is administered intravenously, intramuscularly, intraarterially, intrathecally, intracapsularly, intraorbitally, intradermally, intraperitoneally, transtracheally, subcutaneously, intracerebroventricularly, orally or intranasally.

Exemplary Embodiment 33: The method of any one of Embodiments 30-32, further comprising sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

Exemplary Embodiment 34: The method of any one of Embodiments 30-33, wherein the cancer is associated with detectable PSMA expression in tumors or tumor neovasculature.

Exemplary Embodiment 35: The method of Embodiment 34, wherein the cancer is selected from the group consisting of prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, and stomach cancer.

The invention claimed is:

1. A compound of Formula I, a stereoisomer thereof, or a pharmaceutically acceptable salt of the compound or stereoisomer thereof:

I

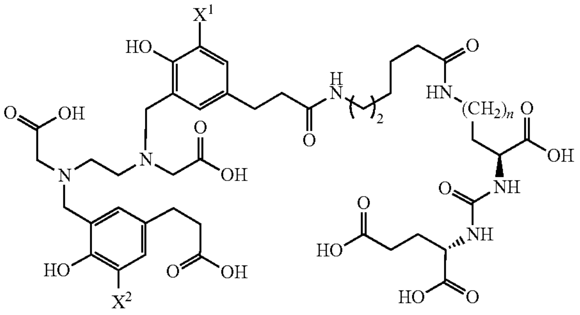

wherein, $X^1$ and $X^2$ are independently selected from the group consisting of H, I, Br, At, a radioisotope of Br (Br*), a radioisotope of I (I*), and a radioisotope of At (At*), provided at least one of $X^1$ and $X^2$ is not H; and n is 1, 2, 3, or 4.

2. The compound of claim 1, wherein the radioisotope of Br*, I* and At* is selected from $^{76}$Br, $^{77}$Br, $^{82}$Br, $^{123}$I, $^{124}$I, $^{125}$I, $^{131}$I, or $^{211}$At.

3. The compound of claim 1, wherein the radioisotope of I* is selected from $^{131}$I or wherein n is 3.

4. The compound of claim 1, wherein both $X^1$ and $X^2$ are a radioisotope of iodine.

5. The compound of claim 1, wherein $X^1$ is I* and $X^2$is H or $X^1$ is H and $X^2$ is I*.

6. The compound of claim 1 , wherein $X^1$ and/or $X^2$ are I*:

IA

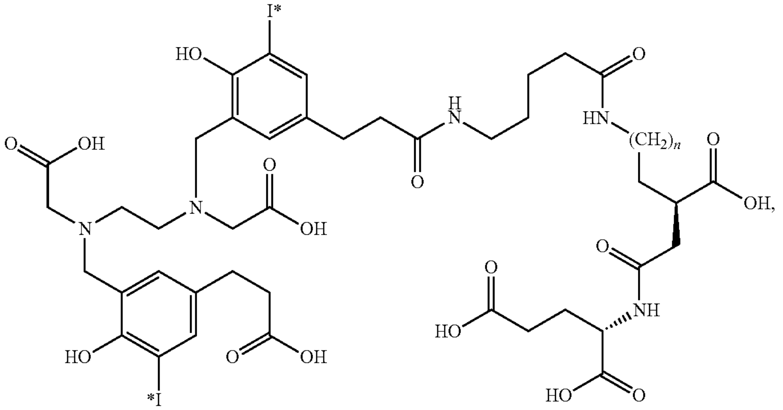

IB

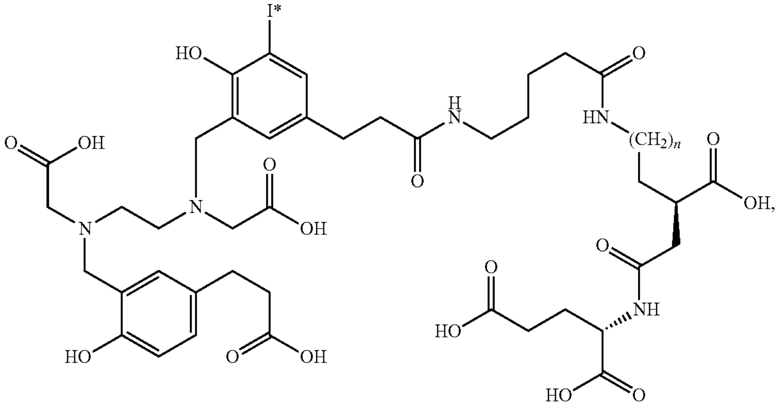

-continued

IC

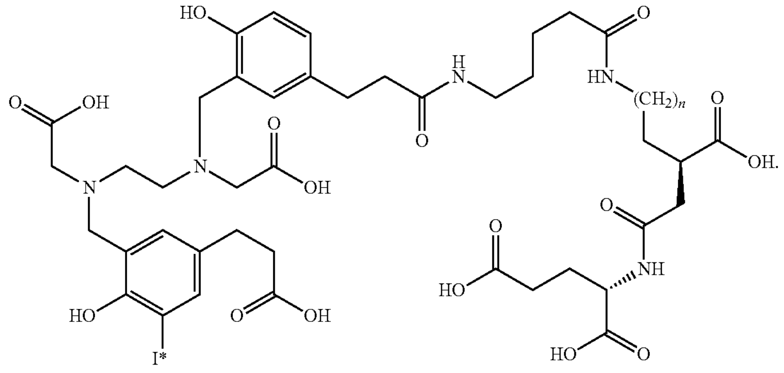

7. A composition comprising two or more compounds of claim 1.

8. A complex comprising a compound of claim 1 and a transition metal, optionally wherein the transition metal is selected from Ga, Fe, Cu, Zn, Sc, Zn, Ti, or a radioisotope thereof.

9. A pharmaceutical composition comprising a pharmaceutical carrier or excipient and a compound of claim 1.

10. The pharmaceutical composition of claim 9 comprising an effective amount of the compound, composition or complex for imaging a cancer associated with detectable PSMA expression in tumors or tumor neovasculature, optionally wherein the cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer; or the imaging is Positron emission tomography (PET), single-photon emission computerized tomography (SPECT), planar imaging, PET/CT, SPECT/CT, multi-nuclide imaging, or any combination thereof.

11. The pharmaceutical composition of claim 9 comprising a therapeutically effective amount of the compound, composition or complex for treating a cancer associated with detectable PSMA expression in tumors or tumor neovasculature, optionally wherein the cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer.

12. A kit comprising a compound of Formula II and an oxidant sufficient to activate iodide, bromide or astatide for labeling of the compound of Formula II, a stereoisomer thereof, or a salt of the compound or stereoisomer:

II

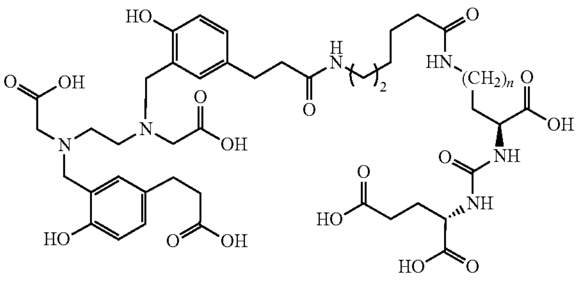

wherein n is 1, 2, 3, or 4, wherein n is 3 and/or wherein the oxidant is chloramine T or 1,3,4,6-tetrachloro-3α,6α-diphenyl glycoluril.

13. A method for detecting solid tumors in a subject in need thereof comprising a. administering an effective amount of the pharmaceutical composition of claim 9 to the subject, wherein the compound, composition or complex is configured to localize to a solid tumor expressing prostate-specific membrane antigen (PSMA); and b. detecting the presence of solid tumors in the subject by detecting radioactive levels emitted by the pharmaceutical composition that are higher than a reference value.

14. A method for selecting a subject for radiation therapy comprising a. administering an effective amount of the pharmaceutical composition of claim 9 to the subject, wherein the compound, composition or complex is configured to localize to a solid tumor expressing prostate-specific membrane antigen (PSMA);

b. detecting radioactive levels emitted by the pharmaceutical composition; and c. selecting the subject for radiation therapy when the radioactive levels emitted by the pharmaceutical composition are higher than a reference value.

15. The method of claim 13, wherein the radioactive levels emitted by the pharmaceutical composition are detected using positron emission tomography, single photon emission computed tomography, planar imaging, PET/CT, SPECT/CT, multi-nuclide imaging, or any combination thereof, or wherein the subject is diagnosed with, or is suspected of having a PSMA-expressing cancer, optionally wherein the PSMA-expressing cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer; or the pharmaceutical composition is administered into the cerebral spinal fluid or blood of the subject; or the pharmaceutical composition is administered intravenously, intramuscularly, intraarterially, intrathecally, intracapsularly, intraorbitally, intradermally, intraperitoneally, transtracheally, subcutaneously, intracerebroventricularly, orally or intranasally; or the radioactive levels emitted by the pharmaceutical composition are detected between 1 to 168 hours after the pharmaceutical composition is administered; or the radioactive levels emitted by the pharmaceutical composition are expressed as the percentage injected dose per gram tissue (% ID/g); or the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

16. The method of claim 14, wherein the radioactive levels emitted by the pharmaceutical composition are detected using positron emission tomography, single photon emission computed tomography, planar imaging, PET/CT, SPECT/CT, multi-nuclide imaging, or any combination thereof; or wherein the subject is diagnosed with, or is suspected of having a PSMA-expressing cancer, optionally wherein the PSMA-expressing cancer is selected from the group consisting of prostate cancer, lung cancer, renal cancer, glioblastoma, pancreatic cancer, bladder cancer, sarcoma, melanoma, breast cancer, colon cancer, a pheochromocytoma, thyroid cancer, esophageal cancer, and stomach cancer; or the pharmaceutical composition is administered into the cerebral spinal fluid or blood of the subject; or the pharmaceutical composition is administered intravenously, intramuscularly, intraarterially, intrathecally, intracapsularly, intraorbitally, intradermally, intraperitoneally, transtracheally, subcutaneously, intracerebroventricularly, orally or intranasally; or the radioactive levels emitted by the pharmaceutical composition are detected between 1 to 168 hours after the pharmaceutical composition is administered; or the radioactive levels emitted by the pharmaceutical composition are expressed as the percentage injected dose per gram tissue (% ID/g); or the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

17. A method for increasing tumor sensitivity to radiation therapy in a subject diagnosed with cancer comprising administering an effective amount of the pharmaceutical composition of claim 9 to the subject, wherein the compound, composition or complex is configured to localize to a solid tumor expressing prostate-specific membrane antigen (PSMA), optionally wherein the pharmaceutical composition is administered intravenously, intramuscularly, intraarterially, intrathecally, intracapsularly, intraorbitally, intradermally, intraperitoneally, transtracheally, subcutaneously, intracerebroventricularly, orally or intranasally; or the cancer is associated with detectable PSMA expression in tumors or tumor neovasculature; or the cancer is selected from the group consisting of prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, and stomach cancer.

18. A method for treating cancer in a subject in need thereof comprising administering an effective amount of the pharmaceutical composition of claim 9 to the subject, wherein the compound, composition or complex is configured to localize to a solid tumor expressing prostate-specific membrane antigen (PSMA), optionally wherein the pharmaceutical composition is administered intravenously, intramuscularly, intraarterially, intrathecally, intracapsularly, intraorbitally, intradermally, intraperitoneally, transtracheally, subcutaneously, intracerebroventricularly, orally or intranasally; or the cancer is associated with detectable PSMA expression in tumors or tumor neovasculature; or the cancer is selected from the group consisting of prostate cancer, lung cancer, renal cancer, glioblastoma, pancreatic cancer, bladder cancer, sarcoma, melanoma, breast cancer, a colon cancer, a pheochromocytoma, thyroid cancer, esophageal cancer, and stomach cancer.

19. The method of claim 18, further comprising sequentially, separately, or simultaneously administering to the subject at least one chemotherapeutic agent selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, proapoptotic agents, methotrexate and CPT-11.

* * * * *